United States Patent
Jensen et al.

(10) Patent No.: US 11,110,110 B2
(45) Date of Patent: *Sep. 7, 2021

(54) CATECHOLAMINE PRODRUGS FOR USE IN THE TREATMENT OF PARKINSON'S DISEASE

(71) Applicant: H. Lundbeck A/S, Valby (DK)

(72) Inventors: Klaus Gjervig Jensen, Valby (DK); Lisbet Kværnø, Valby (DK); Morten Jørgensen, Valby (DK); Martin Juhl, Valby (DK)

(73) Assignee: H. Lundbeck A/S, Valby (DK)

( * ) Notice: Subject to any disclaimer, the term of this patent is extended or adjusted under 35 U.S.C. 154(b) by 0 days.

This patent is subject to a terminal disclaimer.

(21) Appl. No.: 16/872,802

(22) Filed: May 12, 2020

(65) Prior Publication Data

US 2020/0338102 A1      Oct. 29, 2020

Related U.S. Application Data

(63) Continuation of application No. 16/198,917, filed on Nov. 23, 2018, now Pat. No. 10,729,710.

(30) Foreign Application Priority Data

Nov. 24, 2017   (DK) .............. PA201700674

(51) Int. Cl.
| | | |
|---|---|---|
| *A61K 31/706* | (2006.01) | |
| *A61P 25/00* | (2006.01) | |
| *C07D 405/12* | (2006.01) | |
| *C07D 405/14* | (2006.01) | |
| *A61K 31/473* | (2006.01) | |

(52) U.S. Cl.
CPC .......... *A61K 31/706* (2013.01); *A61K 31/473* (2013.01); *A61P 25/00* (2018.01); *C07D 405/12* (2013.01); *C07D 405/14* (2013.01)

(58) Field of Classification Search
None
See application file for complete search history.

(56) References Cited

U.S. PATENT DOCUMENTS

| | | |
|---|---|---|
| 4,543,256 A | 9/1985 | Neumeyer |
| 4,565,818 A | 1/1986 | Nordmann et al. |

(Continued)

FOREIGN PATENT DOCUMENTS

| | | |
|---|---|---|
| CN | 102746351 A | 10/2012 |
| CN | 105218606 A | 1/2016 |

(Continued)

OTHER PUBLICATIONS

International Search Report and Written Opinion for Application No. PCT/EP2018/082361 dated Feb. 22, 2019. 12 pages.

(Continued)

*Primary Examiner* — Traviss C McIntosh, III
(74) *Attorney, Agent, or Firm* — Wolf, Greenfield & Sacks, P.C.

(57) ABSTRACT

The present invention provides compounds of formula (I) that are prodrugs of catecholamine for use in treatment of neurodegenerative diseases and disorders. The present invention also provides pharmaceutical compositions comprising compounds of the invention and methods of treating neurodegenerative or neuropsychiatric diseases and disorders using the compounds of the invention, in particular Parkinson's disease.

Accordingly, the present invention relates to compounds of formula (Id)

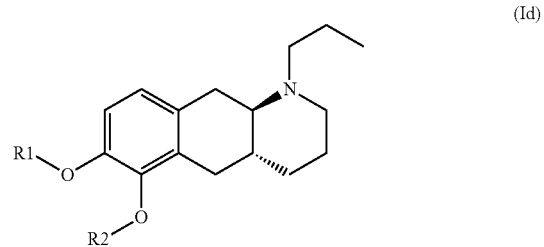

(Id)

wherein
R1 is H and R2 is selected from one of the substituents (i) and (ii) below; or
R1 is selected from one of the substituents (i) and (ii) below and R2 is H; or
R1 and R2 are both represented by substituent (i) below; or
R1 and R2 are both represented by substituent (ii) below; or
R1 is substituent (i) and R2 is substituent (ii); or
R1 is substituent (ii) and R2 is substituent (i);

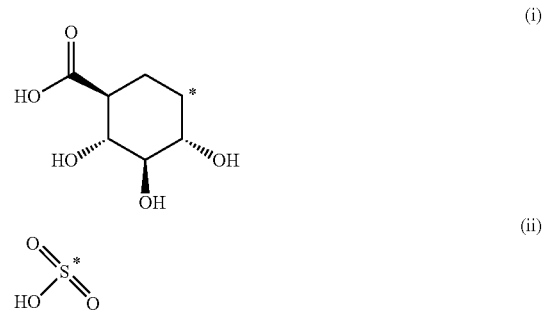

wherein * indicates the attachment point; and
wherein the carbon atom at the attachment point on substituent (i) is in the S-configuration; or a pharmaceutically acceptable salt thereof.

20 Claims, 8 Drawing Sheets

(56) References Cited

U.S. PATENT DOCUMENTS

| | | | |
|---|---|---|---|
| 4,692,453 | A | 9/1987 | Seiler |
| 5,747,513 | A | 5/1998 | Montanari et al. |
| 5,885,988 | A | 3/1999 | Neumann et al. |
| 5,955,468 | A | 9/1999 | Markstein |
| 8,129,530 | B2 | 3/2012 | Jorgensen et al. |
| 10,729,710 | B2 * | 8/2020 | Jensen et al. ........ A61K 31/706 |
| 2009/0062324 | A1 | 3/2009 | Jorgensen et al. |
| 2012/0077836 | A1 | 3/2012 | Wilkstrom et al. |
| 2017/0335357 | A1 | 11/2017 | Divi et al. |
| 2020/0369615 | A1 | 11/2020 | Jacobsen et al. |
| 2020/0369705 | A1 | 11/2020 | Juhl et al. |
| 2020/0369706 | A1 | 11/2020 | Juhl et al. |
| 2020/0392176 | A1 | 12/2020 | Jensen et al. |

FOREIGN PATENT DOCUMENTS

| | | |
|---|---|---|
| GB | 2 192 394 A | 1/1998 |
| JP | S60-172975 A | 9/1985 |
| WO | 90/12574 A1 | 11/1990 |
| WO | 97/03054 A1 | 1/1997 |
| WO | 98/38155 A1 | 9/1998 |
| WO | 00/47571 A1 | 8/2000 |
| WO | 01/36428 A1 | 5/2001 |
| WO | WO 01/76602 A1 | 10/2001 |
| WO | WO 01/78713 A1 | 10/2001 |
| WO | 02/13827 A1 | 2/2002 |
| WO | WO 02/100377 A1 | 12/2002 |
| WO | 03/006458 A1 | 1/2003 |
| WO | 03/013532 A1 | 2/2003 |
| WO | 03/074511 A1 | 9/2003 |
| WO | WO 03/080074 A1 | 10/2003 |
| WO | 2005/062894 A2 | 7/2005 |
| WO | 2006/012640 A2 | 2/2006 |
| WO | WO 2006/056604 A1 | 6/2006 |
| WO | WO 2009/026934 A1 | 3/2009 |
| WO | WO 2009/026935 A1 | 3/2009 |
| WO | WO 2010/097092 A1 | 9/2010 |
| WO | 2013/020979 A1 | 2/2013 |
| WO | WO 2013/034119 A1 | 3/2013 |
| WO | WO 2015/067927 A1 | 5/2015 |
| WO | WO 2017/184871 A1 | 10/2017 |
| WO | 2019/101917 A1 | 5/2019 |

OTHER PUBLICATIONS

Bibbiani et al., Continuous dopaminergic stimulation reduces risk of motor complications in parkinsonian primates. Exp Neurol. Mar. 2005;192(1):73-8.

Alexander et al., Functional architecture of basal ganglia circuits: neural substrates of parallel processing. Trends Neurosci. Jul. 1990;13(7):266-71.

Campbell et al., Behavioral effects of (−)10,11-methylenedioxy-N-n-propylnoraporphine, an orally effective long-acting agent active at central dopamine receptors, and analogous aporphines. Neuropharmacology. Oct. 1982;21(10):953-61.

Cannon et al., N-Alkyl derivatives of trans-6,7-dihydroxy-1,2,3,4,4a,5,10,10b-octahyrobenzo[g]quinoline A congener of apomorphine lacking the non-oxygenated aromatic ring. J. Heterocyclic Chem. Nov. 1980;17:1633-1636.

Cavero et al., Safety Pharmacology assessment of drugs with biased 5-HT(2B) receptor agonism mediating cardiac valvulopathy. J Pharmacol Toxicol Methods. Mar.-Apr. 2014;69(2):150-61. doi: 10.1016/j.vascn.2013.12.004. Epub Dec. 19, 2013.

Delong, Primate models of movement disorders of basal ganglia origin. Trends Neurosci. Jul. 1990;13(7):281-5.

Gerfen et al., D1 and D2 dopamine receptor-regulated gene expression of striatonigral and striatopallidal neurons. Science. Dec. 7, 1990;250(4986):1429-32.

Giardina et al., Adrogolide HCl (ABT-431; DAS-431), a prodrug of the dopamine D1 receptor agonist, A-86929: preclinical pharmacology and clinical data. CNS Drug Rev. 2001 Fall;7(3):305-16.

Goswami et al., Intestinal absorption and metabolism of retinoyl beta-glucuronide in humans, and of 15-[14C]-retinoyl beta-glucuronide in rats of different vitamin A status. J Nutr Biochem. Dec. 2003;14(12):703-9.

Grosset et al., Inhaled dry powder apomorphine (VR040) for 'off' periods in Parkinson's disease: an in-clinic double-blind dose ranging study. Acta Neurol Scand. Sep. 2013;128(3):166-71. doi: 10.1111/ane.12107. Epub Mar. 26, 2013.

Hauser et al., Sublingual apomorphine (APL-130277) for the acute conversion of OFF to ON in Parkinson's disease. Mov Disord. Sep. 2016;31(9):1366-72. doi: 10.1002/mds.26697. Epub Jul. 19, 2016.

Liu et al., A novel synthesis and pharmacological evaluation of a potential dopamine D1/D2 agonist: 1-propyl-1,2,3,4,4a,5,10,10a-octahydrobenzo[g]quinoline-6,7-diol. Bioorg Med Chem. Mar. 15, 2008;16(6):3438-44. doi: 10.1016/j.bmc.2007.06.036. Epub Jun. 23, 2007.

Liu et al., Extremely potent orally active benzo[g]quinoline analogue of the dopaminergic prodrug: 1-propyl-trans-2,3,4,4a,5,7,8,9,10,10a-decahydro-1H-benzo-[g]quinolin-6-one [corrected]. J Med Chem. Feb. 23, 2006;49(4):1494-8. Erratum in: J Med Chem. Nov. 16, 2006;49(23):6930.

Nolen et al., Budesonide-beta-D-glucuronide: a potential prodrug for treatment of ulcerative colitis. J Pharm Sci. Jun. 1995;84(6):677-81.

Poewe et al., Parkinson disease. Nat Rev Dis Primers. Mar. 23, 2017;3:17013. doi: 10.1038/nrdp.2017.13.

Rothman et al., Evidence for possible involvement of 5-HT(2B) receptors in the cardiac valvulopathy associated with fenfluramine and other serotonergic medications. Circulation. Dec. 5, 2000;102(23):2836-41.

Sozio et al., Designing prodrugs for the treatment of Parkinson's disease. Expert Opin Drug Discov. May 2012;7(5):385-406. doi: 10.1517/17460441.2012.677025. Epub Apr. 12, 2012.

Sprenger et al., Management of motor and non-motor symptoms in Parkinson's disease. CNS Drugs. Apr. 2013;27(4):259-72. doi: 10.1007/s40263-013-0053-2.

Stain-Texier et al., Intestinal absorption and stability of morphine 6-glucuronide in different physiological compartments of the rat. Drug Metab Dispos. May 1998;26(5):383-7.

PCT/EP2018/082361, Feb. 22, 2019, International Search Report and Written Opinion.

International Search Report and Written Opinion for Application No. PCT/EP2020/063909 dated Jul. 2, 2020.

International Search Report and Written Opinion for Application No. PCT/EP2020/063910 dated Jul. 14, 2020.

International Search Report and Written Opinion for Application No. PCT/EP2020/063913 dated Jul. 15, 2020.

International Search Report and Written Opinion for Application No. PCT/EP2020/063908 dated Sep. 11, 2020.

Ahari et al., A direct stereoselective approach to trans-2,3-disubstituted piperidines: application in the synthesis of 2-Epi-CP-99,994 and (+)-epilupinine. Org Lett. Jun. 19, 2008;10(12):2473-6. doi: 10.1021/ol800722a. Epub May 14, 2008.

Billeter et al., 8-Hydroxyflavonoid Glucuronides from Malva Sylvestris. Phytochemistry. 1991;30(3):987-90.

Brown et al., Structurally constrained hybrid derivatives containing octahydrobenzo[g or f]quinoline moieties for dopamine D2 and D3 receptors: binding characterization at D2/D3 receptors and elucidation of a pharmacophore model. J Med Chem. Dec. 25, 2008;51(24):7806-19. doi: 10.1021/jm8008629.

Fan et al., Differential effects of pro-BDNF on sensory neurons after sciatic nerve transection in neonatal rats. Eur J Neurosci. May 2008;27(9):2380-90. doi: 10.1111/j.1460-9568.2008.06215.x. Epub Apr. 22, 2008.

Fan et al., Modifications of the isonipecotic acid fragment of SNS-032: analogs with improved permeability and lower efflux ratio. Bioorg Med Chem Lett. Dec. 1, 2008;18(23):6236-9. doi: 10.1016/j.bmcl.2008.09.099. Epub Oct. 2, 2008. (citation on PubMed).

Fumeaux et al., First synthesis, characterization, and evidence for the presence of hydroxycinnamic acid sulfate and glucuronide conjugates in human biological fluids as a result of coffee consumption. Org Biomol Chem. Nov. 21, 2010;8(22):5199-211. doi: 10.1039/c0ob00137f. Epub Sep. 14, 2010.

(56) References Cited

OTHER PUBLICATIONS

Knobloch et al., Keto Esters Derived from 2-(Trimethylsilyl) ethanol: An Orthogonal Protective Group for β-Keto Esters. Synthesis 2008.14 (2008): 2229-2246.
Kotsuki et al., Highly practical, enantiospecific synthesis of the cyclohexyl fragment of the immunosuppressant FK-506. J Org Chem. Aug. 1992;57(18):5036-40.
Loozen et al., An approach to the synthesis of [2] benzopyrano [3, 4?c] pyrroles; alternative dopaminergic molecules. Recueil des Travaux Chimiques des Pays?Bas. 1982;101(9):298-310.
Morissette et al., High-throughput crystallization: polymorphs, salts, co-crystals and solvates of pharmaceutical solids. Adv Drug Deliv Rev. Feb. 23, 2004;56(3):275-300. doi: 10.1016/j.addr.2003.10.020.
Zhang et al., Flavonoid metabolism: the synthesis of phenolic glucuronides and sulfates as candidate metabolites for bioactivity studies of dietary flavonoids. Tetrahedron. Jun. 2012; 68(22):4194-4201.
U.S. Appl. No. 16/876,878, filed May 18, 2020, Published, 2020-0369706.
U.S. Appl. No. 16/876,908, filed May 18, 2020, Published, 2020-0392176.
U.S. Appl. No. 16/876,966, filed May 18, 2020, Published, 2020-0369615.
PCT/EP2020/063909, dated Jul. 2, 2020, International Search Report and Written Opinion.
PCT/EP2020/063910, dated Jul. 14, 2020, International Search Report and Written Opinion.
PCT/EP2020/063913, dated Jul. 15, 2020, International Search Report and Written Opinion.
PCT/EP2020/063908, dated Sep. 11, 2020, International Search Report and Written Opinion.
U.S. Appl. No. 16/198,917, filed Nov. 23, 2018, Granted, U.S. Pat. No. 10,729,710.
U.S. Appl. No. 16/876,843, filed May 18, 2020, Allowed, 2020-0369705.
U.S. Appl. No. 16/876,878, filed May 18, 2020, Allowed, 2020-0369706.
U.S. Appl. No. 16/876,908, filed May 18, 2020, Allowed, 2020-0392176.
U.S. Appl. No. 16/876,966, filed May 18, 2020, Allowed, 2020-0369615.

* cited by examiner

CATECHOLAMINE PRODRUGS FOR USE IN THE TREATMENT OF PARKINSON'S DISEASE

CROSS-REFERENCE TO RELATED APPLICATIONS

This application is a Continuation application of co-pending U.S. application Ser. No. 16/198,917, filed Nov. 23, 2018, which claims Foreign priority benefits under 35 U.S.C. § 119(a)-(d) or 35 U.S.C. § 365(b) of Danish application number PA201700674, filed Nov. 24, 2017. The entire contents of these applications are incorporated herein by reference in their entirety.

FIELD OF THE INVENTION

The present invention provides compounds that are prodrugs of the dopamine agonist (4aR,10aR)-1-n-Propyl-1,2,3,4,4a,5,10,10a-octahydro-benzo[g]quinoline-6,7-diol and their use in the treatment of Parkinson's disease and/or other conditions for which treatment with a dopamine agonist is therapeutically beneficial such as but not limited to Restless leg syndrome, Huntington's disease and Alzheimer's disease; and also neuropsychiatric diseases and disorders such as but not limited to schizophrenia, attention deficit hyperactivity disorder and drug addiction. The present invention also provides pharmaceutical compositions comprising compounds of the invention.

BACKGROUND OF THE INVENTION

Parkinson's disease (PD) is a common neurodegenerative disorder that becomes increasingly prevalent with age, and affects an estimated seven to ten million people worldwide. Parkinson's disease is a multi-faceted disease characterized by both motor and non-motor symptoms. Motor symptoms include resting tremor (shaking), bradykinesia/akinesia (slowness and poverty of movements), muscular rigidity, postural instability and gait dysfunction; whereas non-motor symptoms include neuropsychiatric disorders (e.g. depression, psychotic symptoms, anxiety, apathy, mild-cognitive impairment and dementia) as well as autonomic dysfunctions and sleep disturbances (Poewe et al., Nature Review, (2017) vol 3 article 17013: 1-21).

A key hallmark of Parkinson's disease pathophysiology is the loss of pigmented dopaminergic neurons in the substantia nigra pars compacta that provides dopaminergic innervation to the striatum and other brain areas. Such progressive neurodegeneration leads to the decrease in dopamine striatal levels which ultimately results in a series of changes in the basal ganglia circuitry, ultimately ending up in the occurrence of the four cardinal motor features of Parkinson's disease. The main target of dopamine in the striatum consists of medium spiny GABAergic neurons (MSNs) selectively expressing D1 or D2 receptors pending topographical projections. GABAergic-MSN projecting to the external pallidum, also called striato-pallidal 'indirect pathway' express D2 receptors (MSN-2); whereas GABAergic-MSN projecting to the substantia nigra pars reticulata and internal pallidum, also called striato-nigral 'direct pathway' express D1 receptors (MSN-1). Depletion of dopamine because of neuronal loss results in an imbalanced activity of the two pathways, resulting in a marked reduction of thalamic and cortical output activities and ultimately motor dysfunctions (Gerfen et al, Science (1990) 250: 1429-32; Delong, (1990) Trends in Neuroscience 13: 281-5; Alexander et Crutcher, (1990) Trends in Neuroscience 13: 266-71; and for review Poewe et al., Nature Review (2017) vol. 3 article 17013: 1-21).

The most effective therapeutic strategies available to patients suffering from Parkinson's disease, and aiming at controlling motor symptoms are primarily indirect and direct dopamine agonists. The classic and gold standard treatment regimen includes chronic oral intake of L-3,4-dihydroxy phenylalanine (L-DOPA) which is decarboxylated in the brain to form dopamine. Other approaches consist in the administration of dopamine receptor agonists such as apomorphine which acts both on the D1 and D2 receptors subtypes, or pramipexole, ropinirole and others which are predominantly directed towards D2 receptors subtypes. Optimal motor relief is obtained with use of both L-DOPA and apomorphine due to their activation of both D1 and D2 receptor subtypes and holistic re-equilibrium of the indirect-direct pathways (i.e. while D2 agonists only reverse the indirect pathway dysfunction).

L-DOPA and apomorphine with the structures depicted below are currently the most efficacious PD drugs in clinical use.

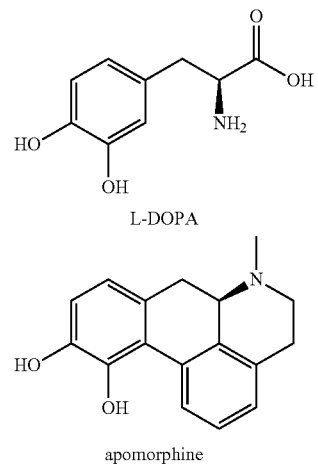

L-DOPA apomorphine

L-DOPA is a prodrug of dopamine and remains the most efficacious drug in the treatment of motor Parkinson's disease. However, after several years of treatment (i.e. honeymoon period), complications arise due the inherent progression of the disease (i.e. sustained loss of dopaminergic neurons) as well as poor pharmacokinetic (PK) profile of L-DOPA. Those complications include [1] dyskinesia which are abnormal involuntary movements occurring during the optimal 'on-time effect' of the drug; and [2] off fluctuations, period during which the L-DOPA positive effect wears off and symptoms re-emerge or worsen (Sprenger and Poewe, CNS Drugs (2013), 27: 259-272).

Direct dopamine receptor agonists are able to activate the dopamine autoreceptors as well as the postsynaptic dopamine receptors located on the medium spiny neurons MSN-1 and MSN-2. Apomorphine belongs to a class of dopamine agonists with a 1,2-dihydroxybenzene (catechol) moiety. When combined with a phenethylamine motif, catecholamines often possess low or no oral bioavailability as is the case for apomorphine. Apomorphine is used clinically in PD therapy albeit with a non-oral delivery (typically intermittent subcutaneous administration or daytime continuous parenteral infusion via a pump). For apomorphine, animal studies have shown that transdermal delivery or implants may provide possible forms of administration. However, when the delivery of apomorphine from implants was studied in monkeys (Bibbiani et al., Chase Experimental Neurology (2005), 192: 73-78) it was found that in most cases the animals had to be treated with the immunosuppressant Dexamethasone to prevent local irritation and other complications following the implantation surgery. Alternative delivery strategies for apomorphine therapy in PD such as inhalation and sublingual formulations have been extensively explored (see e.g. Grosset et al., Acta Neurol Scand. (2013), 128:166-171 and Hauser et al., Movement Disorders (2016), Vol. 32 (9): 1367-1372). However, these efforts are yet not in clinical use for the treatment of PD.

An alternative to the non-oral formulations of the catecholamines involves the use of a prodrug masking the free catechol hydroxyl groups to enable oral administration. However, a known problem associated with the development of prodrugs for clinical use is the difficulties associated with predicting conversion to the parent compound in humans.

Various ester prodrugs of catecholamines have been reported in the literature such as enterically coated N-propyl-apomorphine (NPA) esters for duodenal delivery (see eg. WO 02/100377), and the D1-like agonist Adrogolide, a diacetyl prodrug of A-86929 (Giardina and Williams; CNS Drug Reviews (2001), Vol. 7 (3): 305-316). Adrogolide undergoes extensive hepatic first-pass metabolism in man after oral dosing and, as a result, has a low oral bioavailability (app. 4%). In PD patients, intravenous (IV) Adrogolide has antiparkinson efficacy comparable to that of L-DOPA (Giardina and Williams; CNS Drug Reviews (2001), Vol. 7 (3): 305-316).

In addition to the ester prodrugs of catecholamines, an alternative prodrug approach involves the masking of the two catechol hydroxyl groups as the corresponding methylene-di-oxy (MDO) acetal, as the acetal derived from other aldehydes than formaldehyde, or as the ketal derived from various ketones. This prodrug principle has been described for example in Campbell et al., Neuropharmacology (1982); 21(10): 953-961 and in U.S. Pat. No. 4,543,256, WO 2009/026934 and WO 2009/026935.

Yet another suggested approach for a catecholamine prodrug is the formation of an enone derivative as suggested in for example WO 2001/078713 and in Liu et al., Bioorganic Med. Chem. (2008), 16: 3438-3444. For further examples of catecholamine prodrugs see for example Sozio et al., Exp. Opin. Drug Disc. (2012); 7(5): 385-406.

The compound (4aR,10aR)-1-n-Propyl-1,2,3,4,4a,5,10,10a-octahydro-benzo[g]quinoline-6,7-diol depicted as compound (I) below is disclosed in WO 2009/026934. The trans-isomer was disclosed previously in Liu et al., J. Med. Chem. (2006), 49: 1494-1498 and then in Liu et al., Bioorganic Med. Chem. (2008), 16: 3438-3444 including pharmacological data indicating that the compound has a low oral bioavailability in rats. The racemate was disclosed for the first time in Cannon et al., J. Heterocyclic Chem. (1980); 17: 1633-1636.

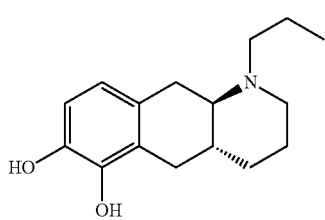

(I)

Compound (I) is a dopamine receptor agonist with mixed D1 and D2 activity. Three prodrug derivatives of compound (I) are known in the art.

Liu et al., J. Med. Chem. (2006), 49: 1494-1498 and Liu et al., Bioorganic Med. Chem. (2008), 16: 3438-3444 disclose the enone derivative of formula (Ia) depicted below which was shown to be converted to the active compound (I) in rats.

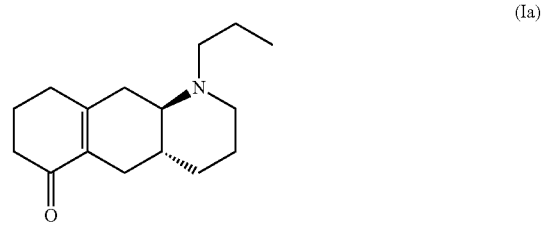

(Ia)

WO 2009/026934 and WO 2009/026935 disclose two types of prodrug derivatives of compound (I) including an MDO derivative with the formula (Ib) below:

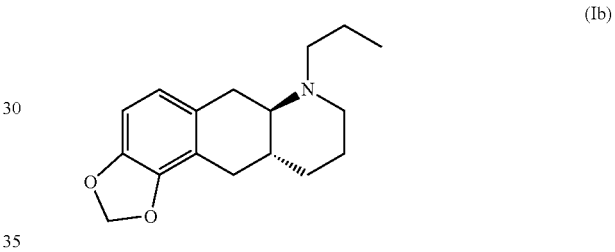

(Ib)

The conversion of compound (Ib) to compound (I) in rat and human hepatocytes has been demonstrated in WO 2010/097092. Furthermore, the in vivo pharmacology of the compounds (Ia) and (Ib) as well as the active "parent compound" (I) has been tested in various animal models relevant for Parkinson's Disease (WO 2010/097092). Both compound (I) and compounds (Ia) and (Ib) were found to be effective, indicating that compounds (Ia) and (Ib) are converted in vivo to compound (I). All three compounds were reported to have a duration of action that was longer than observed for L-dopa and apomorphine.

The other prodrug of compound (I) disclosed in WO 2009/026934 and WO 2009/026935 is a conventional ester prodrug of the formula (Ic):

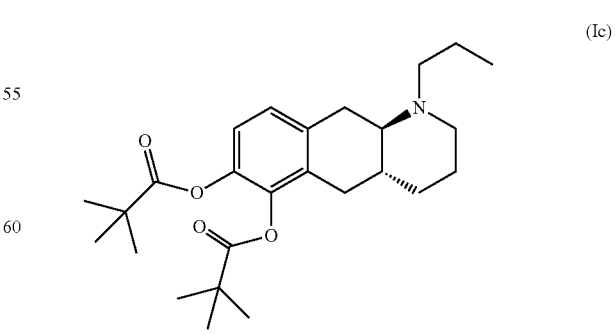

(Ic)

Despite the long-standing interest in the field, there is evidently still an unmet need as regards developing efficient, well-tolerated and orally active drugs for the treatment of PD. A prodrug derivative of a mixed D1/D2 agonist giving a stable PK profile which can provide continuous dopaminergic stimulation may fulfil such unmet needs.

SUMMARY OF THE INVENTION

The present invention relates to new compounds for treatment of Parkinson's Disease. More particularly, the invention relates to new prodrug derivatives of the compound (4aR,10aR)-1-n-Propyl-1,2,3,4,4a,5,10,10a-octahydro-benzo[g]quinoline-6,7-diol (compound (I)). The compounds of the invention have proven particularly useful for oral delivery of compound (I).

Accordingly, the present invention relates to compounds of formula (Id)

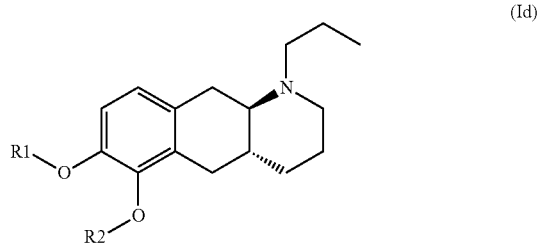

(Id)

wherein
R1 is H and R2 is selected from one of the substituents (i) and (ii) below; or
R1 is selected from one of the substituents (i) and (ii) below and R2 is H; or
R1 and R2 are both represented by substituent (i) below; or
R1 and R2 are both represented by substituent (ii) below; or
R1 is substituent (i) and R2 is substituent (ii); or
R1 is substituent (ii) and R2 is substituent (i);

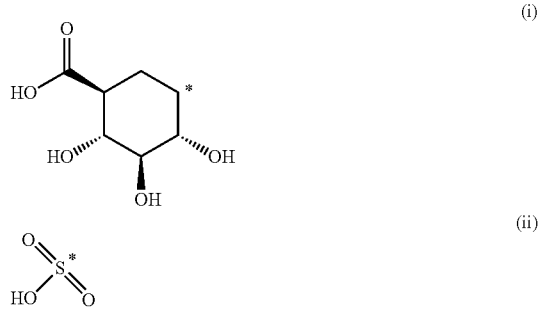

wherein * indicates the attachment point; and
wherein the carbon atom at the attachment point on substituent (i) is in the S-configuration;
or a pharmaceutically acceptable salt thereof.

In one embodiment, the invention relates to a pharmaceutical composition comprising a compound according formula (Id) or a pharmaceutically acceptable salt thereof, and one or more pharmaceutically acceptable excipients.

In one embodiment, the invention relates to a compound according to formula (Id) for use as a medicament.

In one embodiment, the invention relates to a compound according to formula (Id) or a pharmaceutically acceptable salt thereof for use in the treatment of a neurodegenerative disease or disorder such as Parkinson's Disease, Huntington's disease, Restless leg syndrome or Alzheimer's disease; or a neuropsychiatric disease or disorder such as schizophrenia, attention deficit hyperactivity disorder or drug addiction.

In one embodiment, the invention relates to a method for the treatment of a neurodegenerative disease or disorder such as Parkinson's Disease, Huntington's disease, Restless leg syndrome or Alzheimer's disease; or a neuropsychiatric disease or disorder such as schizophrenia, attention deficit hyperactivity disorder or drug addiction; which method comprises the administration of a therapeutically effective amount of a compound of formula (Id) or a pharmaceutically acceptable salt thereof, to a patient in need thereof.

In one embodiment, the invention relates to the use of a compound according to formula (Id) or a pharmaceutically acceptable salt thereof, for the manufacture of a medicament for the treatment of a neurodegenerative disease or disorder such as Parkinson's Disease, Huntington's disease, Restless leg syndrome or Alzheimer's disease; or for the treatment of a neuropsychiatric disease or disorder such as schizophrenia, attention deficit hyperactivity disorder or drug addiction.

In the context of the present invention, it is understood that the carbon atom at the attachment point on substituent (i) is at the anomeric position of (i).

Definitions

Compounds of the Invention

Reference to compounds encompassed by the invention includes the free substance (zwitter ion) of compounds of the invention, pharmaceutically acceptable salts of compounds of the invention, such as acid addition salts or base addition salts, and polymorphic and amorphic forms of compounds of the invention and of pharmaceutically acceptable salts thereof. Furthermore, the compounds of the invention and pharmaceutically acceptable salts thereof may potentially exist in unsolvated as well as in solvated forms with pharmaceutically acceptable solvents such as water, ethanol and the like. Both solvated and unsolvated forms are encompassed by the present invention.

Pharmaceutically Acceptable Salts

Pharmaceutically acceptable salts in the present context is intended to indicate non-toxic, i.e. physiologically acceptable salts.

The term "pharmaceutically acceptable salts" include pharmaceutically acceptable acid addition salts which are salts formed with inorganic and/or organic acids on the nitrogen atom in the parent molecule. Said acids may be selected from for example hydrochloric acid, hydrobromic acid, phosphoric acid, nitrous acid, sulphuric acid, benzoic acid, citric acid, gluconic acid, lactic acid, maleic acid, succinic acid, tartaric acid, acetic acid, propionic acid, oxalic acid, malonic acid, fumaric acid, glutamic acid, pyroglutamic acid, salicylic acid, gentisic acid, saccharin, and sulfonic acids such as methanesulfonic acid, ethanesulfonic acid, toluenesulfonic acid, naphthalene-2-sulphonic acid, 2-hydroxy ethanesulphonic acid and benzenesulfonic acid.

The term pharmaceutically acceptable salts also include pharmaceutically acceptable base addition salts which are salts formed with inorganic and/or organic bases on the acidic groups of compounds of formula (Id). Said bases may be selected from for example zink hydroxide, and alkali metal bases, such as sodium hydroxide, lithium hydroxide, potassium hydroxide, and alkaline earth bases, such as calcium hydroxide and magnesium hydroxide, and organic bases, such as choline, diethylamine, trimethylamine and triethylamine.

Additional examples of useful acids and bases to form pharmaceutically acceptable salts can be found e.g. in Stahl and Wermuth (Eds) "Handbook of Pharmaceutical salts. Properties, selection, and use", Wiley-VCH, 2008.

Solid Form

In the present context, when a compound of the invention is in a solid form, this indicates that said compound is not dissolved in any liquid such as aqueous liquids, organic liquids and mixtures thereof. The invention encompasses solid forms of the free substance (zwitter ion) of compounds of the invention as well as solid forms of pharmaceutically acceptable salts of compounds of the invention. The term "solid form" encompasses both amorphous forms of compounds of the invention and salts thereof and crystalline forms of compounds of the invention and salts thereof.

Prodrug

In the present context, the terms "prodrug" or "prodrug derivative" indicates a compound that, after administration to a living subject, such as a mammal, preferably a human; is converted within the body into a pharmacologically active moiety. The conversion preferably takes place within a mammal, such as in a mouse, rat, dog, minipig, rabbit, monkey and/or human. In the present context a "prodrug of the compound (4aR,10aR)-1-n-Propyl-1,2,3,4,4a,5,10,10a-octahydro-benzo[g]quinoline-6,7-diol" or "a prodrug of the compound of formula (I)" or "a prodrug of compound (I)" is understood to be a compound that, after administration, is converted within the body into the compound (4aR,10aR)-1-n-Propyl-1,2,3,4,4a,5,10,10a-octahydro-benzo[g]quinoline-6,7-diol. Said administration may be by any conventional route of administration of pharmaceutical compositions known in the art, preferably by oral administration.

In the present context, the terms "parent compound" and "parent molecule" indicate the pharmacologically active moiety obtained upon conversion of a corresponding prodrug. For example, the "parent compound" of one of the compounds (Ia), (Ib), (Ic) or any of the compounds of the invention is understood to be the compound of formula (I).

Chemical Manufacturing

In the present context, a compound "derived by chemical manufacturing" indicates that said compound has been manufactured by a chemical process such as, but not limited to, one of the processes described in the experimental section herein.

Pharmacokinetic Definitions and Abbreviations

As used herein, a "PK profile" is an abbreviation of "pharmacokinetic profile". Pharmacokinetic profiles and pharmacokinetic parameters described herein are based on the plasma concentration-time data obtained for the compound of formula (I) after oral dosing of a compound of the invention, using non-compartmental modelling. Abbreviated PK parameters are: $C_{max}$ (maximum concentration); $t_{max}$ (time to $C_{max}$); $t_{1/2}$ (half-life); $AUC_{0-\infty}$ (area under the curve from time of dosing to infinity).

Therapeutically Effective Amount

In the present context, the term "therapeutically effective amount" of a compound means an amount sufficient to alleviate, arrest, partly arrest, remove or delay the clinical manifestations of a given disease and its complications in a therapeutic intervention comprising the administration of said compound. An amount adequate to accomplish this is defined as "therapeutically effective amount". Effective amounts for each purpose will depend e.g. on the severity of the disease or injury as well as the weight and general state of the subject. It will be understood that determining an appropriate dosage may be achieved using routine experimentation, by constructing a matrix of values and testing different points in the matrix, which is all within the ordinary skills of a trained physician.

In the context of the present invention, a "therapeutically effective amount" of a compound of the invention indicates an amount of said compound of the invention that is able to provide an amount of compound (I) that is sufficient to alleviate, arrest, partly arrest, remove or delay the clinical manifestations of a given disease and its complications when said compound of the invention is administered, preferably by the oral route, to a mammal, preferably a human.

Treatment and Treating

In the present context, "treatment" or "treating" is intended to indicate the management and care of a patient for the purpose of alleviating, arresting, partly arresting, removing or delaying progress of the clinical manifestation of the disease. The patient to be treated is preferably a mammal, in particular a human being.

Conditions for Treatment

The compounds of the present invention are intended for treatment of neurodegenerative diseases and disorders such as Parkinson's disease and/or other conditions for which treatment with a dopamine agonist is therapeutically beneficial.

Therapeutic indications include a variety of central nervous system disorders characterized by motor and/or non-motor disturbances and for which part of the underlying pathophysiology is a dysfunction of the striatal-mediated circuitry. Such functional disturbances can be seen in neurodegenerative diseases such as but not limited to Parkinson's disease (PD), Restless leg syndrome, Huntington's disease, and Alzheimer's disease but also neuropsychiatric diseases such as, but not limited to schizophrenia, attention deficit hyperactivity disorder and drug addiction.

In addition to neurodegenerative diseases and disorders, other conditions in which an increase in dopaminergic turnover may be beneficial are in the improvement of mental functions including various aspects of cognition. It may also have a positive effect in depressed patients, and it may also be used in the treatment of obesity as an anorectic agent and in the treatment of drug addiction. It may improve minimal brain dysfunction (MBD), narcolepsy, attention deficit hyperactivity disorder and potentially the negative, the positive as well as the cognitive symptoms of schizophrenia.

Restless leg syndrome (RLS) and periodic limb movement disorder (PLMD) are alternative indications, which are clinically treated with dopamine agonists. In addition, impotence, erectile dysfunction, SSRI induced sexual dysfunction, ovarian hyperstimulation syndrome (OHSS) and certain pituitary tumors (prolactinoma) are also likely to be improved by treatment with dopamine agonists. Dopamine is involved in regulation of the cardiovascular and renal systems, and accordingly, renal failure and hypertension can be considered alternative indications for the compounds of the invention.

The invention encompasses use of the compounds of the invention for treatment of the diseases and disorders listed above.

Combinations

In one embodiment of the invention, the compounds of formula (Id) are for use as stand-alone treatment as the sole active compound. In another embodiment of the invention, the compounds of formula (Id) may be used in combination with other agents useful in the treatment of a neurodegenerative disease or disorder such as Parkinson's disease. The terms "combined use", "in combination with" and "a combination of" and the like as used herein in the context of the method of the invention comprising the combined administration of therapeutically effective amounts of a compound of formula (Id), and another compound, which compound is useful in the treatment a neurodegenerative disease or disorder, is intended to mean the administration of a compound of formula (Id) simultaneously or sequentially, in any order, together with said other compound.

The two compounds may be administered simultaneously or with a time gap between the administrations of the two compounds. The two compounds may be administered either as part of the same pharmaceutical formulation or composition, or in separate pharmaceutical formulations or compositions. The two compounds may be administered on the same day or on different days. They may be administered by the same route, such for example by oral administration, subcutaneous injection, by transdermal administration, by depot, by intramuscular injection or intravenous injection; or by different routes wherein one compound is for example administered orally or placed by depot and the other compound is for example injected. The two compounds may be administered by the same dosage regime or interval, such as once or twice daily, weekly, or monthly; or by different dosage regimes for example wherein one is administered once daily and the other is administered twice daily or weekly or monthly.

In some instances, the patient to be treated may already be in treatment with one or more other compounds useful in the treatment of a neurodegenerative disease or disorder when treatment with a compound of formula (Id) is initiated. In other instances, the patient may already be in treatment with a compound of formula (Id) when treatment with one or more other compounds useful in the treatment of a neurodegenerative disease or disorder is initiated. In other instances, the treatment with a compound of formula (Id) and treatment with one or more other compounds useful in the treatment of a neurodegenerative disease or disorder is initiated at the same time.

Compounds for Combination Treatment

In the context of the invention, compounds to be used in combination with a compound of formula (Id) may be selected from for example L-DOPA, droxidopa, MAO-B inhibitors such as selegiline or rasagiline, COMT inhibitors such as entacapone or tolcapone, adenosine 2a antagonists such as istradefylline, antiglutamatergic agents such as amantadine or memantine, acetylcholinesterase inhibitors such as rivastigmine, donepezil or galantamine and antipsychotic agents such as quetiapine, clozapine, risperidone, pimavanserin, olanzapine, haloperidol, aripiprazole or brexpiprazole.

In addition to small molecules, compounds for combination could also include emerging biologics approaches in treatments for neurodegenerative diseases or disorders such as for example antibodies targeting alpha-synuclein, Tau or A-beta proteins.

Administration Routes

The pharmaceutical compositions comprising a compound of formula (Id), either as the sole active compound or in combination with another active compound, may be specifically formulated for administration by any suitable route such as the oral, rectal, nasal, buccal, sublingual, pulmonal, transdermal and parenteral (e.g. subcutaneous, intramuscular, and intravenous) route. In the context of the present invention the oral route is the preferred route of administration.

It will be appreciated that the route will depend on the general condition and age of the subject to be treated, the nature of the condition to be treated and the active ingredient.

Pharmaceutical Formulations and Excipients

In the following, the term, "excipient" or "pharmaceutically acceptable excipient" refers to pharmaceutical excipients including, but not limited to, carriers, fillers, diluents, antiadherents, binders, coatings, colours, disintegrants, flavours, glidants, lubricants, preservatives, sorbents, sweeteners, solvents, vehicles and adjuvants.

The present invention also provides a pharmaceutical composition comprising a compound of formula (Id), such as one of the compounds disclosed in the Experimental Section herein. The present invention also provides a process for making a pharmaceutical composition comprising a compound of formula (Id). The pharmaceutical compositions according to the invention may be formulated with pharmaceutically acceptable excipients in accordance with conventional techniques such as those disclosed in Remington, "The Science and Practice of Pharmacy", $22^{th}$ edition (2012), Edited by Allen, Loyd V., Jr.

The pharmaceutical composition comprising a compound of the present invention is preferably a pharmaceutical composition for oral administration. Pharmaceutical compositions for oral administration include solid oral dosage forms such as tablets, capsules, powders and granules; and liquid oral dosage forms such as solutions, emulsions, suspensions and syrups as well as powders and granules to be dissolved or suspended in an appropriate liquid.

Solid oral dosage forms may be presented as discrete units (e.g. tablets or hard or soft capsules), each containing a predetermined amount of the active ingredient, and preferably one or more suitable excipients. Where appropriate, the solid dosage forms may be prepared with coatings such as enteric coatings or they may be formulated so as to provide modified release of the active ingredient such as delayed or extended release according to methods well known in the art. Where appropriate, the solid dosage form may be a dosage form disintegrating in the saliva, such as for example an orodispersible tablet.

Examples of excipients suitable for solid oral formulation include, but are not limited to, microcrystalline cellulose, corn starch, lactose, mannitol, povidone, croscarmellose sodium, sucrose, cyclodextrin, talcum, gelatin, pectin, magnesium stearate, stearic acid and lower alkyl ethers of cellulose. Similarly, the solid formulation may include excipients for delayed or extended release formulations known in the art, such as glyceryl monostearate or hypromellose. If solid material is used for oral administration, the formulation may for example be prepared by mixing the active ingredient with solid excipients and subsequently compressing the mixture in a conventional tableting machine; or the formulation may for example be placed in a hard capsule e.g. in powder, pellet or mini tablet form. The amount of solid excipient will vary widely but will typically range from about 25 mg to about 1 g per dosage unit.

Liquid oral dosage forms may be presented as for example elixirs, syrups, oral drops or a liquid filled capsule. Liquid oral dosage forms may also be presented as powders for a solution or suspension in an aqueous or non-aqueous liquid. Examples of excipients suitable for liquid oral formulation include, but are not limited to, ethanol, propylene glycol, glycerol, polyethylenglycols, poloxamers, sorbitol, poly-sorbate, mono and di-glycerides, cyclodextrins, coconut oil, palm oil, and water. Liquid oral dosage forms may for example be prepared by dissolving or suspending the active ingredient in an aqueous or non-aqueous liquid, or by incorporating the active ingredient into an oil-in-water or water-in-oil liquid emulsion.

Further excipients may be used in solid and liquid oral formulations, such as colourings, flavourings and preservatives etc.

Pharmaceutical compositions for parenteral administration include sterile aqueous and nonaqueous solutions, dispersions, suspensions or emulsions for injection or infusion, concentrates for injection or infusion as well as sterile powders to be reconstituted in sterile solutions or dispersions for injection or infusion prior to use. Examples of excipients suitable for parenteral formulation include, but are not limited to water, coconut oil, palm oil and solutions of cyclodextrins. Aqueous formulations should be suitably buffered if necessary and rendered isotonic with sufficient saline or glucose.

Other types of pharmaceutical compositions include suppositories, inhalants, creams, gels, dermal patches, implants and formulations for buccal or sublingual administration.

It is requisite that the excipients used for any pharmaceutical formulation comply with the intended route of administration and are compatible with the active ingredients.

Doses

In one embodiment, the compound of the present invention is administered in an amount from about 0.0001 mg/kg body weight to about 5 mg/kg body weight per day. In particular, daily dosages may be in the range of 0.001 mg/kg body weight to about 1 mg/kg body weight per day. The exact dosages will depend upon the frequency and mode of administration, the sex, the age, the weight, and the general condition of the subject to be treated, the nature and the severity of the condition to be treated, any concomitant diseases to be treated, the desired effect of the treatment and other factors known to those skilled in the art.

A typical oral dosage for adults will be in the range of 0.01-100 mg/day of a compound of the present invention, such as 0.05-50 mg/day, such as 0.1-10 mg/day or 0.1-5 mg/day. Conveniently, the compounds of the invention are administered in a unit dosage form containing said compounds in an amount of about 0.01 to 50 mg, such as 0.05 mg, 0.1 mg, 0.2 mg, 0.5 mg, 1 mg, 5 mg, 10 mg, 15 mg, 20 mg or up to 50 mg of a compound of the present invention.

BRIEF DESCRIPTION OF FIGURES

FIG. 3: X-axis: time (min); Y-axis: Distance travelled (cm)±SEM/5-minute-bins FIG. 4: Y-axis: Total distance travelled (cm)±SEM. Significance levels for post-hoc comparisons (relative to the vehicle group) are indicated: *<0.05, <0.01, *<0.001, ****<0.0001.

DETAILED DESCRIPTION OF THE INVENTION

The inventors have identified new compounds that are prodrugs of (4aR,10aR)-1-n-Propyl-1,2,3,4,4a,5,10,10a-octahydro-benzo[g]quinoline-6,7-diol [compound (I)] which is a dual D1/D2 agonist with in vitro data listed in Table 2.

Figure 1:
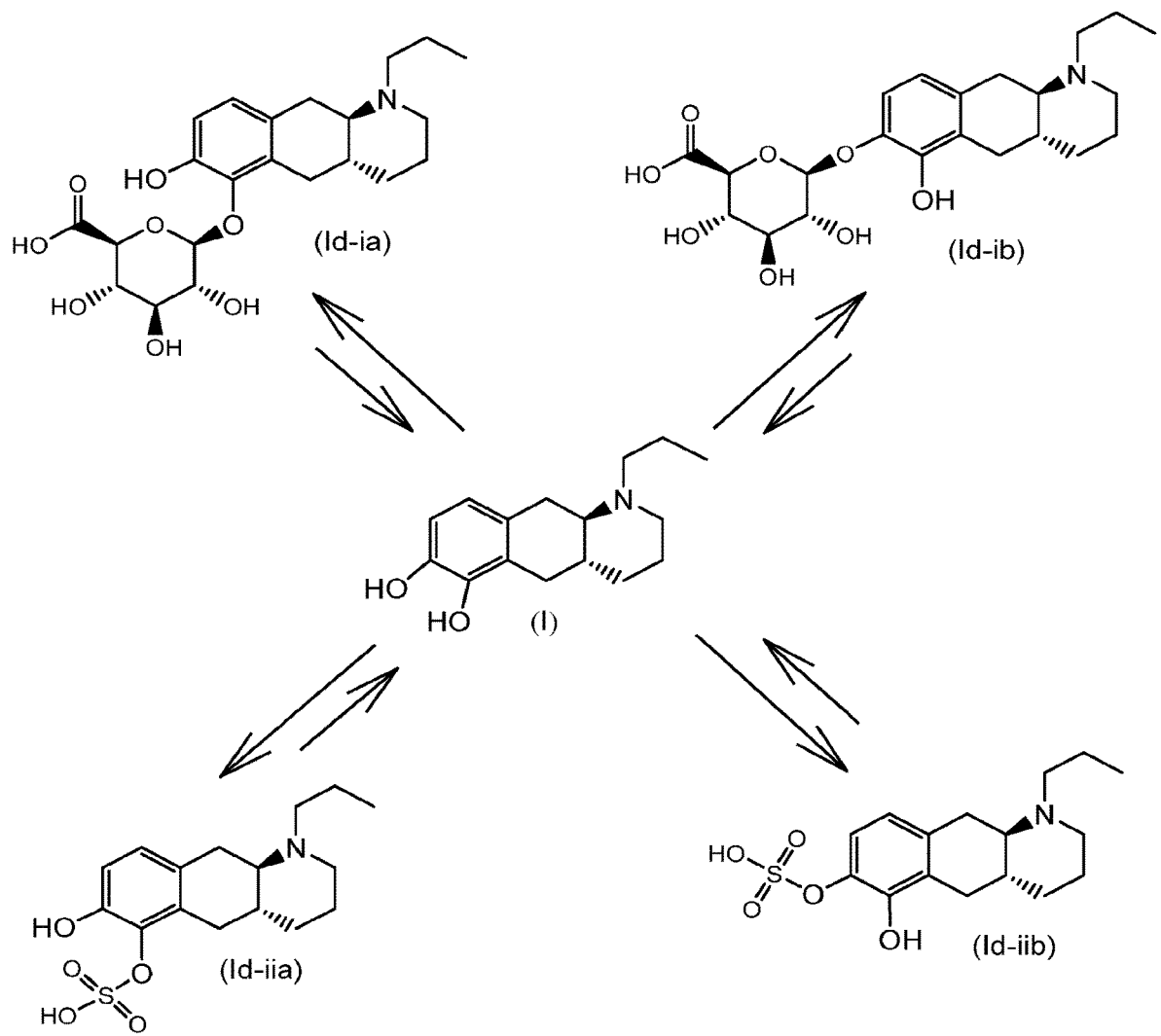
FIG. 1: graphic illustration of conjugation and deconjugation equilibrium in the body between compound (I) and compounds (Id-ia), (Id-ib), (Id-iia) and (Id-iib).

The inventors have observed that compound (I) is conjugated in rat and human hepatocytes to the glucuronide derivatives (Id-ia) and (Id-ib), and the sulfate derivatives (Id-iia) and (Id-iib). The conjugates have shown to be converted to compound (I) by conjugation and de-conjugation in the body as illustrated in FIG. 1.

Glucuronide and sulfate derivatives are commonly known to be unstable in the intestine. The derivatives are formed as highly polar and soluble metabolites to facilitate the elimination of compounds from the body and are consequently easily excreted. For example, in bile duct cannulated rats, glucuronide and sulfate conjugates are often found in bile while their de-conjugate (i.e. the parent compound) is found in faeces. The back-conversion of glucuronide and sulfate conjugates in the intestine to the parent compound which is then sometimes subsequently reabsorbed, is known as part of the enterohepatic re-circulation process. As mentioned earlier, oral dosing of phenethyl catecholamines, such as apomorphine, has generally proven unsuccessful due to low bioavailability. Likewise, compound (I) suffers from low oral bioavailability (Liu et al., Bioorganic Med. Chem. (2008), 16: 3438-3444). With this in mind, and considering the instability of glucuronide and sulfate conjugates in the gastrointestinal tract, it would not be expected that oral dosing of glucuronide and sulfate conjugates of compound (I) can be used to achieve sufficient plasma exposure of the compound.

The principle of applying glucuronide derivatives as prodrugs for oral delivery has been explored for retinoic acid (Goswami et al., J. Nutritional Biochem. (2003) 14: 703-709) and for morphine (Stain-Texier et al., Drug Metab. and Disposition (1998) 26 (5): 383-387). Both studies showed very low exposure levels of the parent compounds after oral dosing of the derivatives. Another study suggests the use of budenoside-ß-D-glucuronide as a prodrug for local delivery of budenoside to the large intestine for treatment of Ulcerative Colitis based on poor absorption of the prodrug itself from the intestinal system (Nolen et al., J. Pharm Sci. (1995), 84 (6): 677-681).

Nevertheless, surprisingly, the inventors of the present invention found that oral dosing of the glucuronide conjugates (Id-ia), (Id-ib) and the sulfate conjugates (Id-iia) and (Id-iib), which have all been identified as metabolites of compound (I) in rats and minipigs provides a systemic exposure of compound (I) in plasma, suggesting the usefulness of glucuronide and sulfate derivatives of compound (I) as orally active prodrugs of compound (I). The inventors further explored the compounds (Id-iab) and (Id-iiab) which are each substituted with either glucuronide or sulfate at both catechol hydroxyl groups, and found that these two compounds also exhibit prodrug activity.

Figure 2:
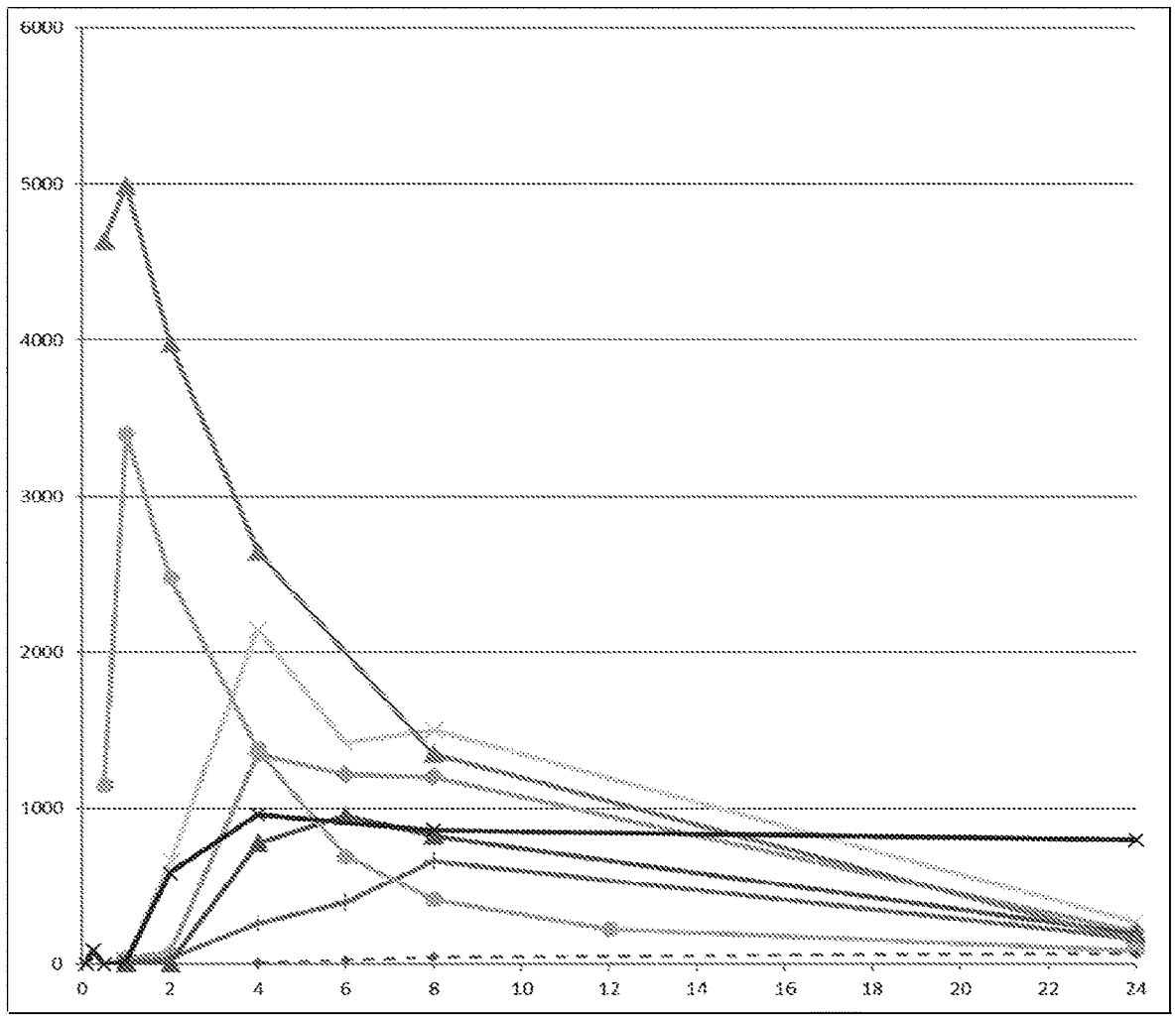
FIG. 2: PK profiles in Wistar rats obtained after oral dosing according to Example 4. Profiles are based on mean plasma concentrations from 3 subjects for each compound. X-axis: time (hours); Y-axis: plasma concentration of Compound (I) (pg/mL) obtained after dosing of the following compounds : ●: compound (Ia) ▲: compound (Ib); ♦: compound (Id-ia); ×: compound (Id-ib); ▲: compound (Id-iia); +: compound (Id-iib), X: compound (Id-iab) and ♦: compound (Id-iiab).

The plasma profiles of compound (I) resulting from oral dosing of compounds (Ia) and (Ib) and of each of the compounds (Id-ia), (Id-ib), (Id-iia), (Id-iib), (Id-iab) and (Id-iiab) to Wistar rats according to Example 4 are shown in FIG. 2. For all the compounds, the doses were corrected by molecular weight to equal a dose of 300 µg/kg of compound (Ib) corresponding to 287 µg/kg of compound (I). The inventors have found that oral dosing of compounds (Ia) and (Ib) to Wistar rats results in early and high peak concentrations of compound (I). Such high peak concentrations are in humans likely to be associated with dopaminergic side effects such as for example nausea, vomiting and light headedness. In contrast, dosing of the compounds (Id-ia), (Id-ib), (Id-iia), (Id-iib); (Id-iab) and (Id-iiab) results in a slower absorption rate avoiding rapid peak concentrations accompanied by a sustained exposure of compound (I) in plasma. Additionally, the plasma exposure of compound (I) in Wistar rats is maintained throughout 24 hours although the obtained AUC of compound (I) is generally lower than the AUC obtained after dosing of compound (Ib). However, since the peak concentrations of compound (I) which are expected to drive the side effects are lower, higher doses might be administered of the compounds (Id-ia), (Id-ib), (Id-iia), (Id-iib), (Id-iab) and (Id-iiab) to potentially achieve higher overall plasma concentrations of compound (I) compared to what is achievable from dosing compounds (Ia) and (Ib). When investigating PK properties of compound (Ic), the inventors found that the plasma concentrations of compound (I) were extremely low, leaving compound (Ic) unsuitable as a prodrug of compound (I) for oral administration and confirming that the oral bioavailability of the compounds of the invention is highly unpredictable. PK parameters for the PK studies in Wistar rats are listed in Table 3.

PK experiments have also been performed with oral dosing of compounds (Id-ia), (Id-ib), (Id-iia) and (Id-jib) to minipigs according to Example 5. The study demonstrated that all the four compounds are converted to compound (I) in minipigs and provides plasma exposure of compound (I) after oral dosing. PK parameters for this study are listed in Table 4.

Figure 7A:
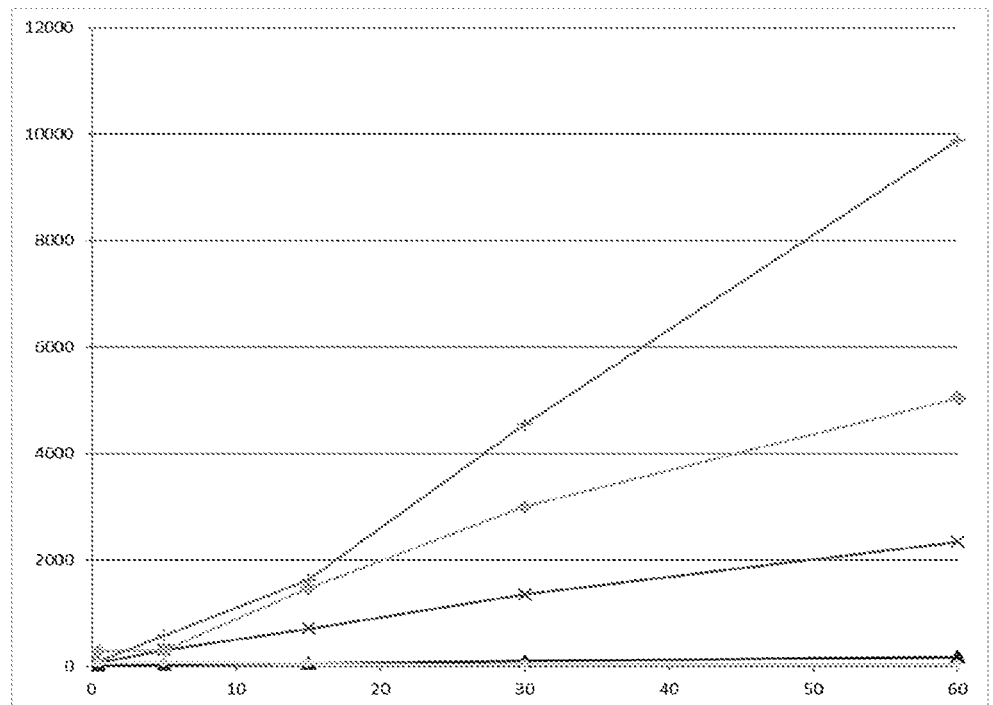
FIG. 7: conversion of compounds (Id-ia), (Id-ib), (Id-iia), (Id-iib) and (Id-iab) to compound (I) in rat (7a) and human (7b) hepatocytes. X-axis time (min); Y-axis: concentration of compound (I) (pg/mL). ♦: compound (Id-Ia); ×X: compound (Id-ib); ▲: compound (Id-iia); +: compound (Id-iib); ♦: compound (Id-iab).
Figure 7B:
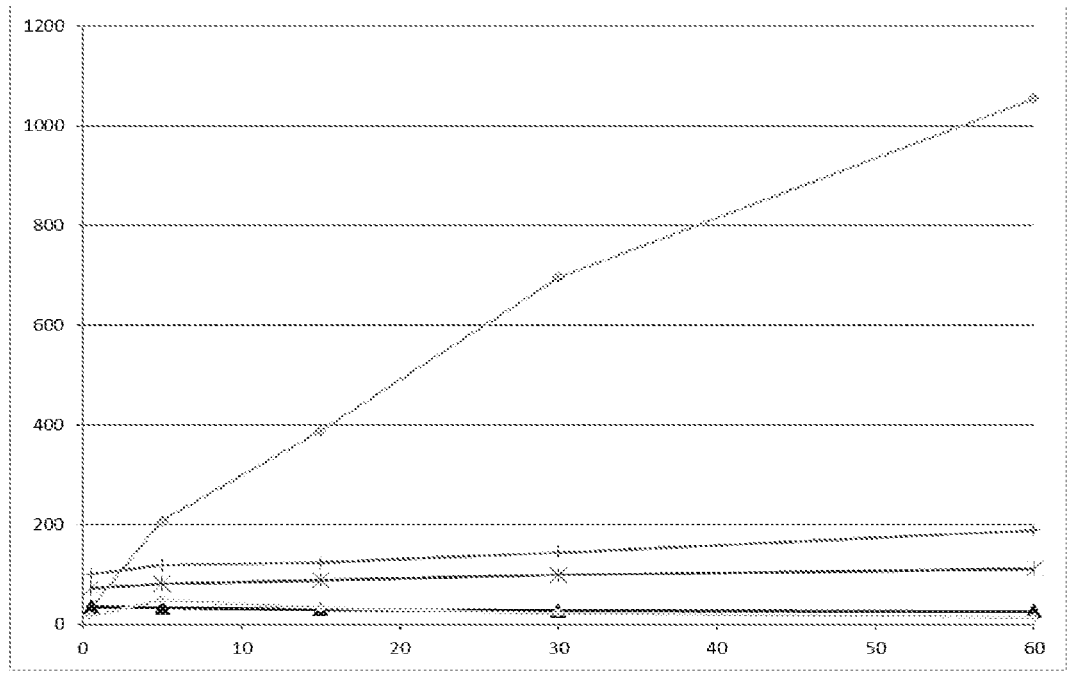
Figure 8A:
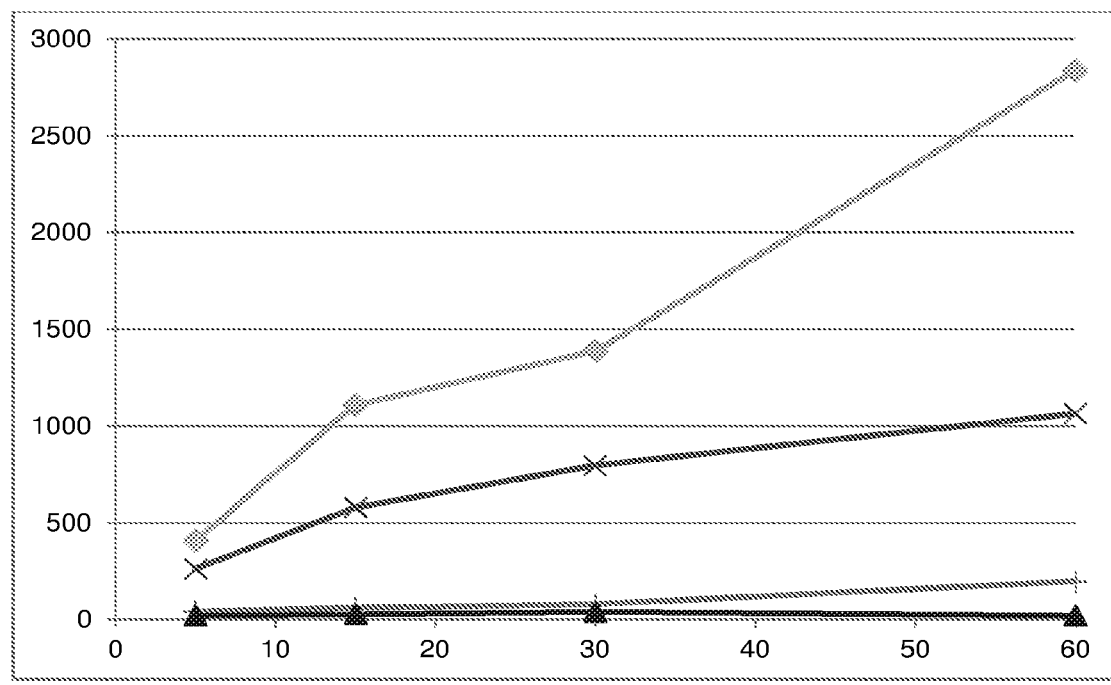
FIG. 8: conversion of compounds (Id-ia), (Id-ib), (Id-iia) and (Id-iib) to compound (I) in rat (8a) and human (8b) whole blood. X-axis time (min); Y-axis: concentration of compound (I) (pg/mL). ♦: compound (Id-ia); ×: compound (Id-ib); ▲: compound (Id-iia); compound (Id-iib).
Figure 8B:
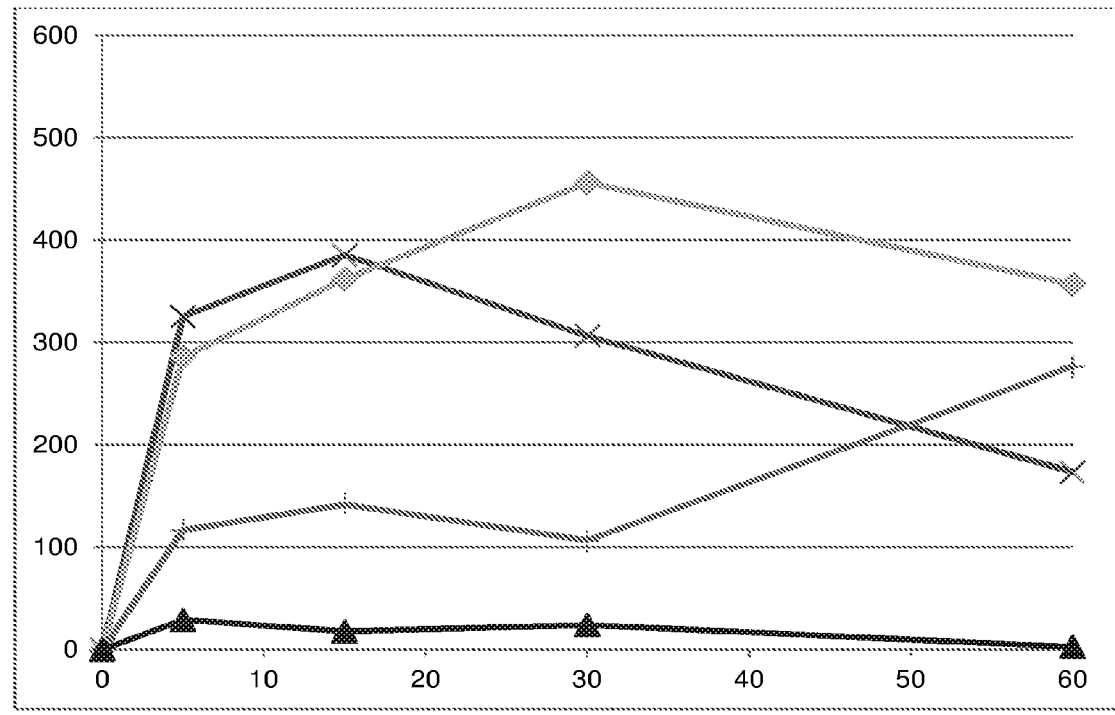

Bioconversion of the compounds (Id-ia), (Id-ib), (Id-iia), (Id-iib) and (Id-iab) in human is supported by the Experiments of Example 1 indicating conversion of the compounds to the compound of formula (I) in rat and human hepatocytes and for (Id-ia), (Id-ib), (Id-iia), (Id-iib) in rat and human blood (FIGS. 7 and 8).

Thus, in conclusion, the compounds of the invention are useful as orally active prodrugs of compound (I) and has been observed in rats to provide a PK profile avoiding the peak $C_{max}$ observed for the known prodrugs (Ia) and (Ib) and providing a significantly higher AUC of compound (I) than compound (Ic). Preferred compounds of the invention are the glucuronide conjugates (Id-ia), (Id-ib) and (Id-iab).

As a comparative example, one glucuronide and two sulfate conjugates of apomorphine ((2S,3S,4S,5R,6S)-6-[[(6aR)-11-hydroxy-6-methyl-5,6,6a,7-tetrahydro-4H-dibenzo[de,g]quinolin-10-yl]oxy]-3,4,5-trihydroxy-tetrahydro-pyran-2-carboxylic acid; [(6aR)-11-hydroxy-6-methyl-5,6,6a,7-tetrahydro-4H-dibenzo[de,g]quinolin-10-yl] hydrogen sulfate, and [(6aR)-10-hydroxy-6-methyl-5,6,6a,7-tetrahydro-4H-dibenzo[de,g]quinolin-11-yl] hydrogen sulfate) were dosed to Wistar rats. Dosing the conjugates of apomorphine orally to Wistar rat at doses as high as 4977 µg/kg, did not result in measurable exposure of apomorphine in plasma (lower limit of quantification 500 pg/ml) except for 916 pg/ml at one time point (4 h) from dosing the glucuronide conjugate indicating low/no oral bioavailability of the conjugates of apomorphine. In comparison, oral dosing of 3000 µg/kg apomorphine itself resulted in plasma AUC>100-fold lower than seen after subcutaneous administration of 3000 µg/kg apomorphine, confirming the known poor oral bioavailability of apomorphine. This further supports that the oral availability of the compounds of the invention is highly unexpected (for experimental, see Example 4).

Figure 3:
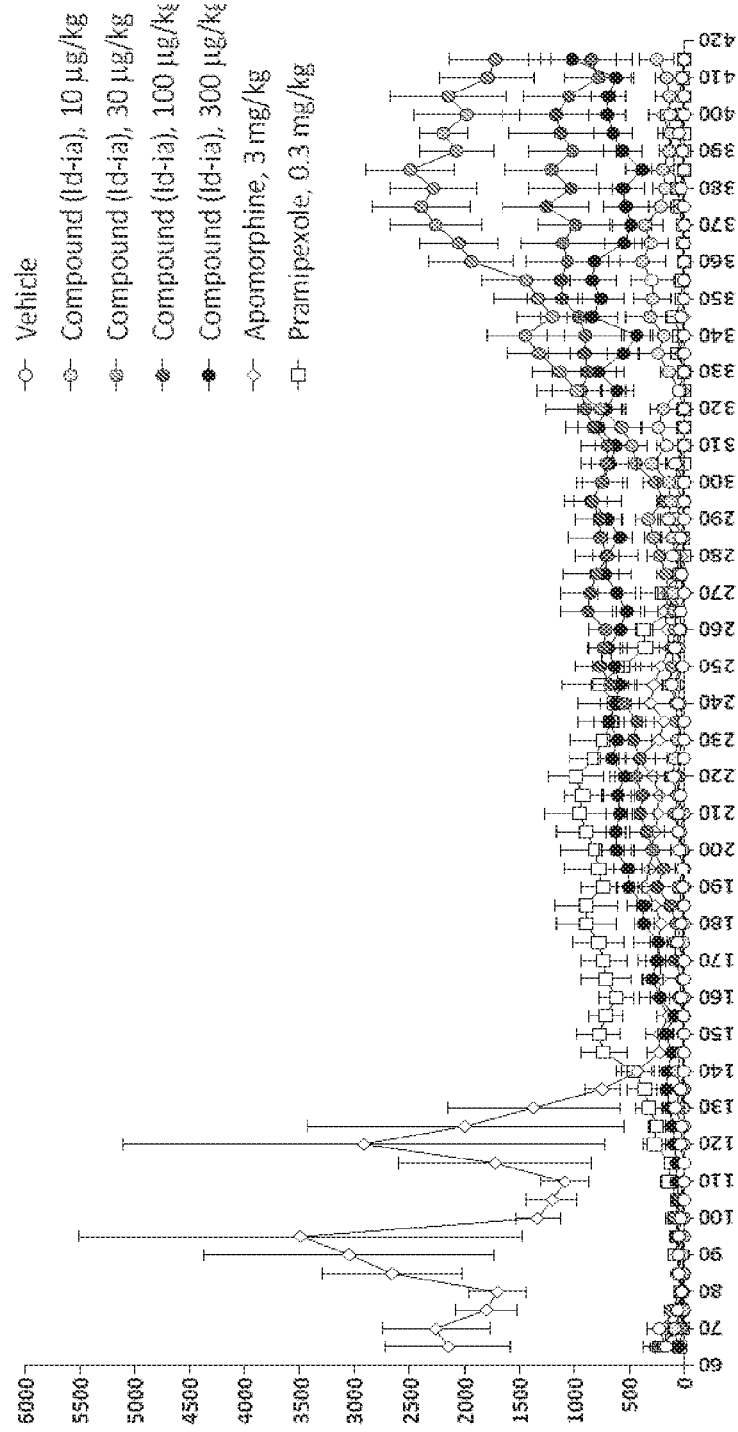
FIGS. 3 and 4: Locomotor activity time-course (FIG. 3) and total distance travelled (FIG. 4) following treatment with vehicle ($H_2O$, p.o.), or compound (Id-ia) (10, 30, 100 or 300 µg/kg, p.o.) and compared to standard-of-care (SoC) treatments: apomorphine (APO, 3 mg/kg, s.c.), pramipexole (PPX, 0.3 mg/kg, s.c.). Animals were dosed at t=60 minutes after a 60-min. habituation period in test chambers, and activity was monitored for 350 minutes thereafter. Data was evaluated by use of a Kruskal-Wallis test with Dunn's Multiple Comparisons test, resulting in an overall P-value of <0.0001.
Figure 4:
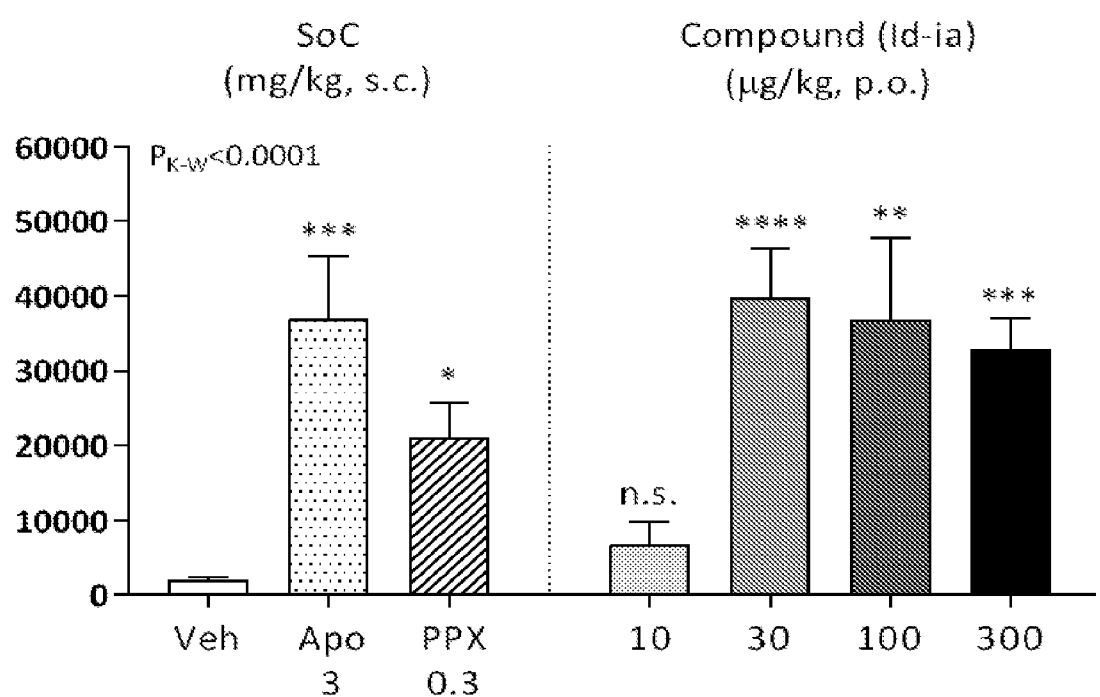
Figure 5:
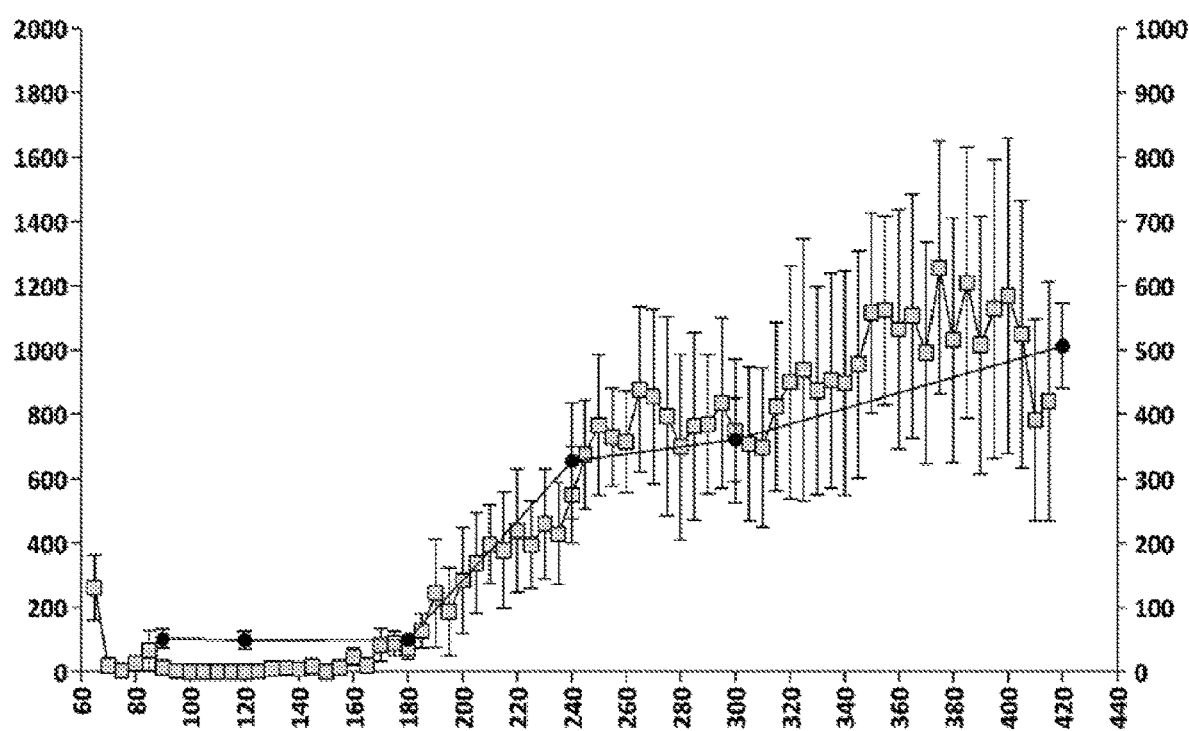
FIGS. 5 and 6: Relationships between plasma concentrations of compound (Id-ia) and compound (I) and hyperactivity induced by compound (Id-ia) (100 µg/kg, p.o.) (FIG. 5) and the corresponding relationship between plasma apomorphine concentrations and hyperactivity induced by apomorphine (3 mg/kg, s.c.) (FIG. 6). X-axis time (min); Y-axis left: Distance travelled (cm)±SEM/5-minute-bins; Y-axis right (FIG. 5): plasma concentration of compound (I) (pg/mL); Y axis right (FIG. 6): plasma concentration of apomorphine (ng/mL). □: Distance travelled (cm) ● plasma-concentration.

Compound (Id-ia) has further been explored in the rat locomotor activity assay according to Example 6. The assay demonstrated a dopaminergic effect obtained after oral administration of compound (Id-ia) c.f. FIGS. 3, 4 and 5. The fact that the compounds of the invention including (Id-ia) possess no in vitro dopaminergic activity c.f. example 2 and table 1, further indicates that the effect of compound (Id-ia) in the rat locomotor activity assay is obtained by conversion of compound (Id-ia) to compound (I).

Finally, an important issue associated with the prior art compound (Ib) is that this compound is an agonist of the 5-HT2B receptor. Since 5-HT2B receptor agonists have been linked to pathogenesis of valvular heart disease (VHD) after long term exposure, such compounds are not suitable for use in the treatment of chronical diseases (Rothman et al., Circulation (2000), 102: 2836-2841; and Cavero and Guillon, J. Pharmacol. Toxicol. Methods (2014), 69: 150-161). Thus, a further advantage of the compounds of the invention is that these are not 5-HT2B agonists c.f. example 3 and Table 1.

The compounds of the invention are useful in the treatment of neurodegenerative diseases and disorders such as Parkinson's disease and/or other conditions for which treatment with a dopamine agonist is therapeutically beneficial. The compounds, being suitable for oral administration have the potential of providing a new treatment paradigm in Parkinson's Disease.

In one embodiment of the invention, the compounds are for use as stand-alone treatment of a neurodegenerative disease or disorder. In another embodiment of the invention, the compounds are to be used in combination with other agents for treatment of PD such as a compound selected from the group consisting of L-DOPA, a MAO-B inhibitor such as selegiline or rasagiline, a COMT inhibitor such as entacapone or tolcapone, an adenosine 2a antagonist such as istradefylline, an antiglutamatergic agent such as amantadine or memantine, an acetylcholinesterase inhibitor such as rivastigmine, donepezil or galantamine, an antipsychotic agent such as quetiapine, clozapine, risperidone, pimavanserin, olanzapine, haloperidol, aripiprazole or brexpiprazole; or in combination with an antibody targeting alpha-synuclein, Tau or A-beta protein.

Embodiments of the Invention

In the following, embodiments of the invention are disclosed. The first embodiment is denoted E1, the second embodiment is denoted E2 and so forth E1. A compound according to formula (Id)

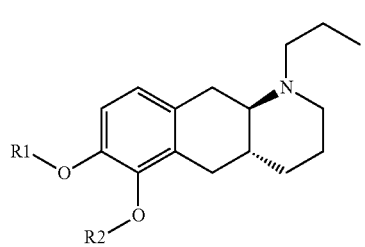

(Id)

wherein
R1 is H and R2 is selected from one of the substituents (i) and (ii) below; or
R1 is selected from one of the substituents (i) and (ii) below and R2 is H; or R1 and R2 are both represented by substituent (i) below; or
R1 and R2 are both represented by substituent (ii) below; or
R1 is substituent (i) and R2 is substituent (ii); or
R1 is substituent (ii) and R2 is substituent (i);

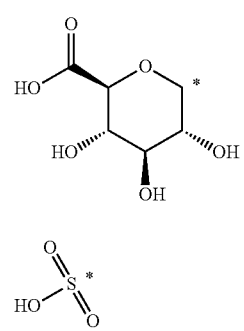

(i)

(ii)

wherein * indicates the attachment point; and
wherein the carbon atom at the attachment point on substituent (i) is in the S-configuration;
or a pharmaceutically acceptable salt thereof.

E2. The compound or pharmaceutically acceptable salt thereof according to embodiment 1, wherein
R1 is H and R2 is selected from one of the substituents (i) and (ii); or
R1 is selected from one of the substituents (i) and (ii) and R2 is H; or
R1 and R2 are both represented by substituent (i); or
R1 and R2 are both represented by substituent (ii).

E3. The compound or pharmaceutically acceptable salt thereof according to embodiment 1, wherein R1 is H and R2 is substituent (i); or
R1 is substituent (i) and R2 is H; or
R1 and R2 are both represented by substituent (i).

E4. The compound according to embodiment 1, wherein said compound is the compound represented by formula (Id-ia) below

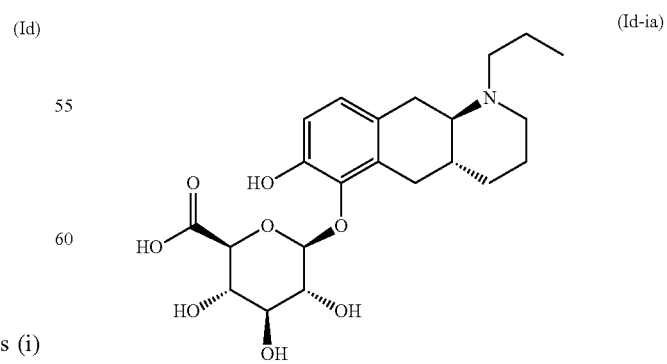

(Id-ia)

or a pharmaceutically acceptable salt thereof.

E5. The compound according to embodiment 1, wherein said compound is the compound represented by formula (Id-ib) below

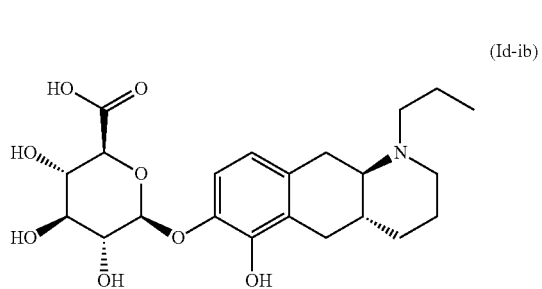 [SMILES: CCCN1CCC[C@@H]2Cc3c(ccc(O[C@@H]4O[C@H](C(=O)O)[C@@H](O)[C@H](O)[C@H]4O)c3O)C[C@H]21]

or a pharmaceutically acceptable salt thereof.

E6. The compound according to embodiment 1, wherein said compound is the compound represented by formula (Id-iab) below

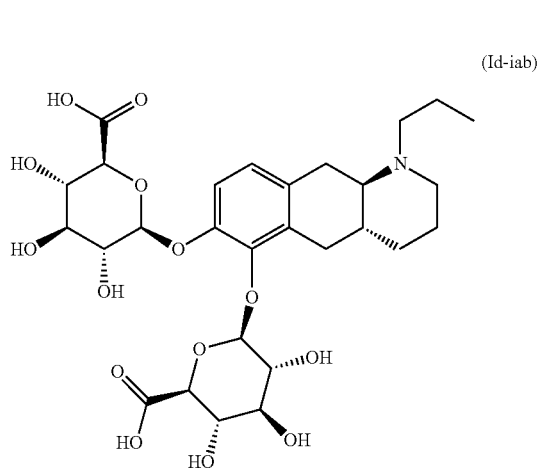 [SMILES: CCCN1CCC[C@@H]2Cc3c(ccc(O[C@@H]4O[C@H](C(=O)O)[C@@H](O)[C@H](O)[C@H]4O)c3O[C@@H]3O[C@H](C(=O)O)[C@@H](O)[C@H](O)[C@H]3O)C[C@H]21]

or a pharmaceutically acceptable salt thereof.

E7. The compound or pharmaceutically acceptable salt thereof according to embodiment 1, wherein R1 is H and R2 is substituent (ii); or R1 is substituent (ii) and R2 is H; or R1 and R2 are both represented by substituent (ii).

E8. The compound according to embodiment 1, wherein said compound is the compound represented by formula (Id-iia) below

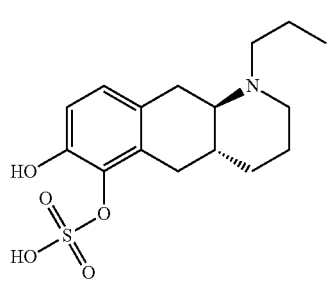

or a pharmaceutically acceptable salt thereof.

E9. The compound according to embodiment 1, wherein said compound is the compound represented by formula (Id-jib) below

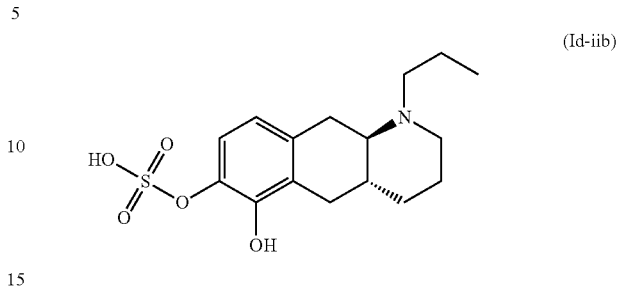

or a pharmaceutically acceptable salt thereof.

E10. The compound according to embodiment 1, wherein said compound is the compound represented by formula (Id-iiab) below

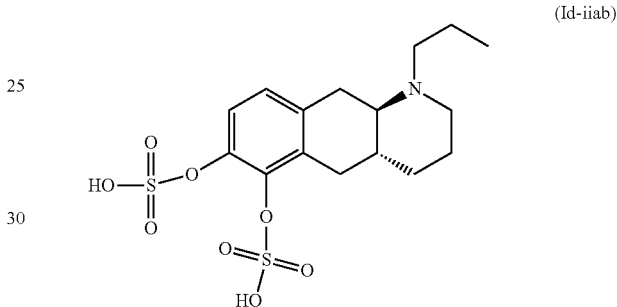

or a pharmaceutically acceptable salt thereof.

E11. The compound according to embodiment 1, wherein the compound is selected from the group consisting of:

(Id-ia): (2S,3S,4S,5R,6S)-3,4,5-trihydroxy-6-(((4aR,10aR)-7-hydroxy-1-propyl-1,2,3,4,4a,5,10,10a-octahydrobenzo[g]quinolin-6-yl)oxy)tetrahydro-2H-pyran-2-carboxylic acid;

(Id-ib): (2S,3S,4S,5R,6S)-3,4,5-trihydroxy-6-(((4aR,10aR)-6-hydroxy-1-propyl-1,2,3,4,4a,5,10,10a-octahydrobenzo[g]quinolin-7-yl)oxy)tetrahydro-2H-pyran-2-carboxylic acid;

(Id-iia): (4aR,10aR)-7-hydroxy-1-propyl-1,2,3,4,4a,5,10,10a-octahydrobenzo[g]quinolin-6-yl hydrogen sulfate;

(Id-iib): (4aR,10aR)-6-hydroxy-1-propyl-1,2,3,4,4a,5,10,10a-octahydrobenzo[g]quinolin-7-yl)hydrogen sulfate;

(Id-iab): (2S,2'S,3S,3'S,4S,4'S,5R,5'R,6',6'S)-6,6'-(((4aR,10aR)-1-propyl-1,2,3,4,4a,5,10,10a- octahydrobenzo[g]quinoline-6,7-diy)bis(oxy))bis(3,4,5-trihydroxytetrahydro-2H-pyran-2-carboxylic acid);

(Id-iiab): (4aR,10aR)-1-propyl-1,2,3,4,4a,5,10,10a-octahydrobenzo[g]quinoline-6,7-diyl bis(hydrogen sulfate);

or a pharmaceutically acceptable salt of any of these compounds.

E12. The compound or pharmaceutically acceptable salt thereof according to any of embodiments 1-11, wherein said compound is derived outside the body of a mammal.

E13. The compound or pharmaceutically acceptable salt thereof according to any of embodiments 1-12, wherein said compound is derived by chemical manufacturing.

E14. The compound or pharmaceutically acceptable salt thereof according to any of embodiments 1-13, wherein said compound is on an isolated form.

E15. The compound or pharmaceutically acceptable salt thereof according to any of embodiments 1-14, wherein said compound is on an isolated form substantially free of compounds within which it is naturally in equilibrium.

E16. The compound or pharmaceutically acceptable salt thereof according to any of embodiments 1-15, wherein said compound is on an isolated form substantially free of the compound of formula (I).

E17. A compound which is a prodrug of the compound (4aR,10aR)-1-n-Propyl-1,2,3,4,4a,5,10,10a-octahydro-benzo[g]quinoline-6,7-diol (compound (I)), wherein said prodrug provides a PI<profile wherein $C_{max}$ of (4aR,10aR)-1-n-Propyl-1,2,3,4,4a,5,10,10a-octahydro-benzo[g]quinoline-6,7-diol is between 500 and 2500 pg/mL, such as between 750 and 2500 pg/mL, such as between 1000 and 2500 pg/mL, such as between 1000 and 2000 pg/mL when said prodrug is administered orally to a Wistar rat in a dose corresponding to 287 µg/kg of (4aR,10aR)-1-n-Propyl-1,2,3,4,4a,5,10,10a-octahydro-benzo[g]quinoline-6,7-diol; or a pharmaceutically acceptable salt of said compound.

E18. The compound or pharmaceutically acceptable salt thereof according to embodiment 17, which is a prodrug of the compound (4aR,10aR)-1-n-Propyl-1,2,3,4,4a,5,10,10a-octahydro-benzo[g]quinoline-6,7-diol (compound (I)), wherein said prodrug provides a PK profile wherein AUC0-∞ of (4aR,10aR)-1-n-Propyl-1,2,3,4,4a,5,10,10a-octahydro-benzo[g]quinoline-6,7-diol is more than 7000 pg*h/mL, such as more than 8000, such as more than 9000, such as more than 10000, such as more than 11000, such as more than 12000, such as more than 13000, such as more than 14000, such as more than 15000, such as more than 16000 pg*h/mL when said prodrug is administered orally to a Wistar rat in a dose corresponding to 287 mg/kg of (4aR,10aR)-1-n-Propyl-1,2,3,4,4a,5,10,10a-octahydro-benzo[g]quinoline-6,7-diol.

E19. The compound or pharmaceutically acceptable salt thereof according to any of embodiments 17-18, wherein said PK profile has been obtained by a PK experiment as described in Example 4 herein.

E20. The compound or pharmaceutically acceptable salt thereof according to any of embodiments 1-19, wherein said compound or pharmaceutically acceptable salt thereof is in a solid form.

E21. A pharmaceutically acceptable salt of a compound according to any of embodiments 1-20.

E22. The pharmaceutically acceptable salt according to embodiment 21, wherein said salt is an acid addition salt of a compound according to any of embodiments 1-20.

E23. The pharmaceutically acceptable salt according to embodiment 21, wherein said salt is a base addition salt of a compound according to any of embodiments 1-20.

E24. The compound or pharmaceutically acceptable salt thereof according to any of embodiments 1-23, for use in therapy.

E25. A compound or pharmaceutically acceptable salt thereof according to any of embodiments 1-23, for use as a medicament.

E26. The compound or pharmaceutically acceptable salt for use as a medicament according to embodiment 25, wherein said medicament is an oral medicament such as a tablet or a capsule for oral administration.

E27. A pharmaceutical composition comprising a therapeutically effective amount of the compound or pharmaceutically acceptable salt thereof according to any of embodiments 1-23, and one or more pharmaceutically acceptable excipients.

E28. The pharmaceutical composition according to embodiment 27, wherein said pharmaceutical composition is for oral administration.

E29. The pharmaceutical composition according to any of embodiments 27-28, wherein said pharmaceutical composition is an oral pharmaceutical composition.

E30. The pharmaceutical composition according to any of embodiments 27-29, wherein said pharmaceutical composition is a solid oral dosage form.

E31. The pharmaceutical composition according to any of embodiments 27-30, wherein said pharmaceutical composition is a tablet or a capsule for oral administration.

E32. The pharmaceutical composition according to any of embodiments 27-31, wherein said pharmaceutical composition further comprises another agent which is useful in the treatment of a neurodegenerative disease or disorder such as Parkinson's disease.

E33. The pharmaceutical composition according to any of embodiments 27-31, wherein said pharmaceutical composition further comprises a compound selected from the group consisting of L-DOPA, a MAO-B inhibitor such as selegiline or rasagiline, a COMT inhibitor such as entacapone or tolcapone, an adenosine 2a antagonist such as istradefylline, an antiglutamatergic agent such as amantadine or memantine, an acetylcholinesterase inhibitor such as rivastigmine, donepezil or galantamine, an antipsychotic agent such as quetiapine, clozapine, risperidone, pimavanserin, olanzapine, haloperidol, aripiprazole or brexpiprazole; or an antibody targeting alpha-synuclein, Tau or A-beta protein.

E34. A compound or pharmaceutically acceptable salt thereof according to any of embodiments 1-23, for use in the treatment of a neurodegenerative disease or disorder such as Parkinson's Disease, Huntington's disease, Restless leg syndrome or Alzheimer's disease; or a neuropsychiatric disease or disorder such as schizophrenia, attention deficit hyperactivity disorder or drug addiction.

E35. The compound or pharmaceutically acceptable salt thereof according to any of embodiments 1-23, for use in the treatment according to embodiment 34, wherein said neurodegenerative disease or disorder is Parkinson's Disease.

E36. The compound or pharmaceutically acceptable salt thereof according to any of embodiments 1-23, for use in the treatment according to any of embodiments 34-35, wherein said compound is to be used in combination with another agent which is useful in the treatment of a neurodegenerative disease or disorder such as Parkinson's disease.

E37. The compound or pharmaceutically acceptable salt thereof according to any of embodiments 1-23, for use in the treatment according to any of embodiments 34-35, wherein said compound is to be used in combination with a compound selected from the group consisting of L-DOPA, a MAO-B inhibitor such as selegiline or rasagiline, a COMT inhibitor such as entacapone or tolcapone, an adenosine 2a antagonist such as istradefylline, an antiglutamatergic agent such as amantadine or memantine, an acetylcholinesterase inhibitor such as rivastigmine, donepezil or galantamine, an antipsychotic agent such as quetiapine, clozapine, risperidone, pimavanserin, olanzapine, haloperidol, aripiprazole or brexpiprazole; or in combination with an antibody targeting alpha-synuclein, Tau or A-beta protein.

E38. The compound or pharmaceutically acceptable salt thereof according to any of embodiments 1-23, for use in the treatment according to any of embodiments 34-37, wherein said treatment is performed by oral administration of said compound.

E39. The compound or pharmaceutically acceptable salt thereof according to any of embodiments 1-23, for use in the treatment according to any of embodiments 34-38, wherein said compound is comprised in an oral pharmaceutical composition such as a tablet or a capsule for oral administration.

E40. A method for the treatment of a neurodegenerative disease or disorder such as Parkinson's Disease, Huntington's disease, Restless leg syndrome or Alzheimer's disease; or a neuropsychiatric disease or disorder such as schizophrenia, attention deficit hyperactivity disorder or drug addiction; which method comprises the administration of a therapeutically effective amount of a compound or pharmaceutically acceptable salt thereof according to any of embodiments 1-23, to a patient in need thereof.

E41. The method according to embodiment 40, wherein said neurodegenerative disease or disorder is Parkinson's Disease.

E42. The method according to any of embodiments 40-41, wherein said compound or pharmaceutically acceptable salt thereof according to any of embodiments 1-23, is used in combination with another agent which is useful in the treatment of a neurodegenerative disease or disorder such as Parkinson's disease.

43. The method according to any of embodiments 40-41, wherein said compound or pharmaceutically acceptable salt thereof according to any of embodiments 1-23, is used in combination with a compound selected from the group consisting of L-DOPA, a MAO-B inhibitor such as selegiline or rasagiline, a COMT inhibitor such as entacapone or tolcapone, an adenosine 2a antagonist such as istradefylline, an antiglutamatergic agent such as amantadine or memantine, an acetylcholinesterase inhibitor such as rivastigmine, donepezil or galantamine, an antipsychotic agent such as quetiapine, clozapine, risperidone, pimavanserin, olanzapine, haloperidol, aripiprazole or brexpiprazole; or in combination with an antibody targeting alpha-synuclein, Tau or A-beta protein.

E44. The method according to any of embodiments 40-43, wherein said administration is performed by the oral route.

E45. The method according to any of embodiments 40-44, wherein said compound or pharmaceutically acceptable salt thereof according to any of embodiments 1-23 is comprised in an oral pharmaceutical composition such as a tablet or a capsule for oral administration.

E46. Use of a compound or pharmaceutically acceptable salt thereof according to any of embodiments 1-23, in the manufacture of a medicament for the treatment of a neurodegenerative disease or disorder such as Parkinson's Disease, Huntington's disease, Restless leg syndrome or Alzheimer's disease; or for the treatment of a neuropsychiatric disease or disorder such as schizophrenia, attention deficit hyperactivity disorder or drug addiction.

E47. The use according to embodiment 46, wherein said neurodegenerative disease or disorder is Parkinson's Disease.

E48. The use according to any of embodiments 46-47, wherein said medicament is used in combination with another agent which is useful in the treatment of a neurodegenerative disease or disorder such as Parkinson's disease.

E49. The use according to any of embodiments 46-47, wherein said medicament is used in combination with a compound selected from the group consisting of L-DOPA, a MAO-B inhibitor such as selegiline or rasagiline, a COMT inhibitor such as entacapone or tolcapone, an adenosine 2a antagonist such as istradefylline, an antiglutamatergic agent such as amantadine or memantine, an acetylcholinesterase inhibitor such as rivastigmine, donepezil or galantamine, an antipsychotic agent such as quetiapine, clozapine, risperidone, pimavanserin, olanzapine, haloperidol, aripiprazole or brexpiprazole; or in combination with an antibody targeting alpha-synuclein, Tau or A-beta protein.

E50. The use according to any of embodiments 46-49, wherein said medicament is an oral medicament such as a tablet or a capsule for oral administration.

In the context of the present invention, it is understood that the carbon atom at the attachment point on substituent (i) (depicted in embodiment 1) is at the anomeric position of (i).

All references, including publications, patent applications and patents, cited herein are hereby incorporated by reference in their entirety and to the same extent as if each reference were individually and specifically indicated to be incorporated by reference and were set forth in its entirety (to the maximum extent permitted by law).

Headings and sub-headings are used herein for convenience only, and should not be construed as limiting the invention in any way.

The description herein of any aspect or aspect of the invention using terms such as "comprising", "having," "including" or "containing" with reference to an element or elements is intended to provide support for a similar aspect or aspect of the invention that "consists of", "consists essentially of" or "substantially comprises" that particular element or elements, unless otherwise stated or clearly contradicted by context (e.g., a composition described herein as comprising a particular element should be understood as also describing a composition consisting of that element, unless otherwise stated or clearly contradicted by context).

The use of any and all examples, or exemplary language (including "for instance", "for example", "e.g.", and "as such") in the present specification is intended merely to better illuminate the invention, and does not pose a limitation on the scope of invention unless otherwise indicated.

It should be understood that the various aspects, embodiments, implementations and features of the invention mentioned herein may be claimed separately, or in any combination.

The present invention includes all modifications and equivalents of the subject-matter recited in the claims appended hereto, as permitted by applicable law.

Compounds of the Invention

TABLE 1

Exemplified compounds of the invention

| Example | Compound |
|---------|----------|
| (Id-ia) | (2S,3S,4S,5R,6S)-3,4,5-trihydroxy-6-(((4aR,10aR)-7-hydroxy-1-propyl-1,2,3,4,4a,5,10,10a-octahydrobenzo[g]quinolin-6-yl)oxy)tetrahydro-2H-pyran-2-carboxylic acid |
| (Id-ib) | (2S,3S,4S,5R,6S)-3,4,5-trihydroxy-6-(((4aR,10aR)-6-hydroxy-1-propyl-1,2,3,4,4a,5,10,10a-octahydrobenzo[g]quinolin-7-yl)oxy)tetrahydro-2H-pyran-2-carboxylic acid |

TABLE 1-continued

Exemplified compounds of the invention

| Example | Compound |
| --- | --- |
| (Id-iia) | (4aR,10aR)-7-hydroxy-1-propyl-1,2,3,4,4a,5,10,10a-octahydrobenzo[g]quinolin-6-yl hydrogen sulfate |
| (Id-iib) | (4aR,10aR)-6-hydroxy-1-propyl-1,2,3,4,4a,5,10,10a-octahydrobenzo[g]quinolin-7-yl hydrogen sulfate |
| (Id-iab) | (2S,2'S,3S,3'S,4S,4'S,5R,5'R,6S,6'S)-6,6'-(((4aR,10aR)-1-propyl-1,2,3,4,4a,5,10,10a-octahydrobenzo[g]quinoline-6,7-diyl)bis(oxy))bis(3,4,5-trihydroxytetrahydro-2H-pyran-2-carboxylic acid) |
| Id-iiab | (4aR,10aR)-1-propyl-1,2,3,4,4a,5,10,10a-octahydrobenzo[g]quinoline-6,7-diyl bis(hydrogen sulfate) |

Experimental Section

Preparation of the Compounds of the Invention

The compounds of formula (Id) may be prepared by methods described below, together with synthetic methods known in the art of organic chemistry, or modifications that are familiar to those of ordinary skill in the art. The starting materials used herein are available commercially or may be prepared by routine methods known in the art, such as those methods described in standard reference books such as "Compendium of Organic Synthetic Methods, Vol. I-XII" (published with Wiley-Interscience). Preferred methods include, but are not limited to, those described below.

The schemes are representative of methods useful in synthesizing the compounds of the present invention. They are not intended to constrain the scope of the invention in any way.

LC-MS Methods

Analytical LC-MS data were obtained using the methods identified below.

Method 550: LC-MS were run on Waters Aquity UPLC-MS consisting of Waters Aquity including column manager, binary solvent manager, sample organizer, PDA detector (operating at 254 nM), ELS detector, and TQ-MS equipped with APPI-source operating in positive ion mode.

LC-conditions: The column was Acquity UPLC BEH C18 1.7 μm; 2.1×50 mm operating at 60° C. with 1.2 ml/min of a binary gradient consisting of water+0.05% trifluoroacetic acid (A) and acetonitrile/water (95:5)+0.05% trifluoroacetic acid.

Gradient:

| | |
| --- | --- |
| 0.00 min | 10% B |
| 1.00 min | 100% B |
| 1.01 min | 10% B |
| 1.15 min | 10% B |

Total run time: 1.15 min

Method 551: LC-MS were run on Waters Aquity UPLC-MS consisting of Waters Aquity including column manager, binary solvent manager, sample organizer, PDA detector (operating at 254 nM), ELS detector, and TQ-MS equipped with APPI-source operating in positive ion mode.

LC-conditions: The column was Acquity UPLC HSS T3 1.8 μm; 2.1×50 mm operating at 60° C. with 1.2 ml/min of a binary gradient consisting of water+0.05% trifluoroacetic acid (A) and acetonitrile/water (95:5)+0.05% trifluoroacetic acid.

Gradient:

| | |
| --- | --- |
| 0.00 min | 2% B |
| 1.00 min | 100% B |
| 1.15 min | 2% B |

Total run time: 1.15 min

Method 555: LC-MS were run on Waters Aquity UPLC-MS consisting of Waters Aquity including column manager, binary solvent manager, sample organizer, PDA detector (operating at 254 nM), ELS detector, and TQ-MS equipped with APPI-source operating in positive ion mode.

LC-conditions: The column was Acquity UPLC BEH C18 1.7 μm; 2.1×150 mm operating at 60° C. with 0.6 ml/min of a binary gradient consisting of water+0.05% trifluoroacetic acid (A) and acetonitrile/water (95:5)+0.05% trifluoroacetic acid.

Gradient:

| | |
| --- | --- |
| 0.00 min | 10% B |
| 3.00 min | 100% B |
| 3.60 min | 10% B |

Total run time: 3.6 min

Method 111: LC-MS were run on a Shimadzu LCMS-2020 consisting of PDA detector operating at 190-800 nM and MS equipped with ESI source operating in positive mode.

LC-conditions: The column was Phenomenex Kinetex EVO C18 2.6 Elm; 2.1×100 mm operating at 25° C. with 0.5 ml/min of a gradient consisting of water+0.1% formic acid (A) and acetonitrile+0.1% formic acid (B).

Gradient:

| | |
| --- | --- |
| 0.00 min | 2% B |
| 1.00 min | 2% B |
| 10.00 min | 90% B |
| 13.00 min | 90% B |
| 13.10 min | 2% B |
| 18.00 min | 2% B |

Total run time: 18 min

Method 222: LC-MS were run on a Shimadzu LCMS-2020 consisting of PDA detector operating at 190-800 nM and MS equipped with ESI source operating in positive mode. LC-conditions: The column was Phenomenex Kinetex EVO C18 2.6 Lim; 2.1×100 mm operating at 25° with 0.5 ml/min of a gradient consisting of water+0.1% formic acid (A) and acetonitrile (B).

Gradient:

| | |
|---|---|
| 0.00 min | 2% B |
| 1.00 min | 2% B |
| 10.00 min | 90% B |
| 13.00 min | 90% B |
| 13.10 min | 2% B |
| 18.00 min | 2% B |

Total run time: 18 min
Preparative LCMS was performed using the method identified below.
Waters AutoPurification system using combined mass/UV detection.
Column: Sunfire 30×100 mm, 5 um particles. Operating at 40° C. with 90 ml/min of a binary gradient consisting of water+0.05% trifluoroacetic acid (A) and acetonitrile/water (3:5)+0.05% trifluoroacetic acid.
Gradient:

| | |
|---|---|
| 0.00 min | 98% A |
| 5.00 min | 50% A |
| 5.50 min | 98% A |
| 6.00 min | 98% A |

HighRes MS was run on a Bruker Compact qTOF equipped with electrospray operating in positive or negative mode. Direct infusion was used and calibration was done with sodium formate.

Preparation of Compounds of the Invention—General Methods

Compound (I) which can for example be prepared as disclosed in WO 2009/026934 was used as an intermediate in the synthesis of compounds of the invention. In brief, compound (Id-ia) and (Id-ib) of the invention can be prepared from (I) by reacting (I) with triisopropylsilyl chloride in the presence of DIPEA (N,N-Diisopropylethylamine) in dichloromethane affording a mixture of mono silylated intermediates (4aR,10aR)-1-propyl-7-((triisopropylsilyl)oxy)-1,2,3,4,4a,5,10,10a-octahydrobenzo[g]quinolin-6-ol and (4aR,10aR)-1-propyl-6-((triisopropylsilyl)oxy)-1,2,3,4,4a,5,10,10a-octahydrobenzo[g]quinolin-7-ol, which were subsequently subjected to protection with a tert-butyloxycarbonyl protecting group Boc-protection, affording intermediates tert-butyl ((4aR,10aR)-1-propyl-7-((triisopropylsilyl)oxy)-1,2,3,4,4a,5,10,10a-octahydrobenzo[g]quinolin-6-yl) carbonate [A] and tert-butyl ((4aR,10aR)-1-propyl-6-((triisopropylsilypoxy)-1,2,3,4,4a,5,10,10a-octahydrobenzo[g]quinolin-7-yl) carbonate [B Subsequent removal of the silyl group, using TEA-3HF (Triethylamine trihydrofluoride), and reprotection using acetyl anhydride, can be performed to afford a mixture of (4aR,10aR)-6-((tert-butoxycarbonyl)oxy)-1-propyl-1,2,3,4,4a,5,10,10a-octahydrobenzo[g]quinolin-7-yl acetate and (4aR,10aR)-7-((tert-butoxycarbonyl)oxy)-1-propyl-1,2,3,4,4a,5,10,10a-octahydrobenzo[g]quinolin-6-ylacetate. A glucuronide coupling can then be made using tetra-acetate coupling donor ((2S,3R,4S,5S,6S)-6-(methoxycarbonyl)tetrahydro-2H-pyran-2,3,4,5-tetrayl tetraacetate) in the presence of boron trifluoride diethyl etherate (BF$_3$-OEt$_2$) as the Lewis acid catalyst, to afford a mixture of the desired coupling adducts (2S,3R,4S,5S,6S)-2-(((4aR,10aR)-7-acetoxy-1-propyl-1,2,3,4,4a,5,10,10a-octahydrobenzo[g]quinolin-6-yl)oxy)-6-(methoxycarbonyl)tetrahydro-2H-pyran-3,4,5-triyl triacetate and (2S,3R,4S,5S,6S)-2-W4aR,10aR)-6-acetoxy-1-propyl-1,2,3,4,4a,5,10,10a-octahydrobenzo[g]quinolin-7-yl)oxy)-6-(methoxycarbonyl)tetrahydro-2H-pyran-3,4,5-triyl triacetate. The crude mixture can then be subjected to hydrolysis using KCN in wet methanol to afford (Id-ia) and (Id-ib) which can be separated by column chromatography. In brief, compound (Id-iia) and (Id-iib) of the invention can be prepared from (I) (by reacting (I) with pyridine sulfur trioxide complex in pyridine providing a mixture of mono sulfates (Id-iia) and (Id-iib) which can be separated be column chromatography.

Exemplified Compounds of the Invention (Id-iia): (4aR,10aR)-7-hydroxy-1-propyl-1,2,3,4,4a,5,10,10a-octahydrobenzo[g]quinolin-6-yl hydrogen sulfate, and
(Id-iib): (4aR,10aR)-6-hydroxy-1-propyl-1,2,3,4,4a,5,10,10a-octahydrobenzo[g]quinolin-7-yl hydrogen sulfate.

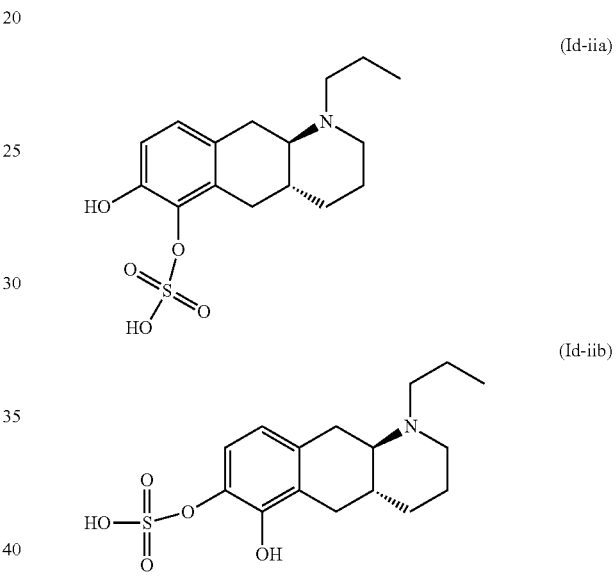

(4aR,10aR)-1-propyl-1,2,3,4,4a,5,10,10a-octahydrobenzo[g]quinoline-6,7-diol, Hydrochloride (1.51 g) was suspended in pyridine (25 ml) under nitrogen atmosphere at room temperature, pyridine sulfur trioxide complex (2.31 g) was added and the suspension was stirred at room temperature. After 15 h and 23 h, additional pyridine sulfur trioxide complex (2×(2.1 g, 13.1 mmol)) were added and the mixture stirred at room temperature overnight.

After stirring for a total of two days, the crude mixture was diluted with MeOH/dichloromethane and evaporated directly on filter aid. Purification by column chromatography (eluent: ethyl acetate/triethylamine/MeOH, 95:5:0-70:5:25), afforded a ca. 3:1 ratio of the two sulfates. The mixture was suspended in 10 mL MeOH, 50 mL water was slowly added and the resulting suspension was stirred at room temperature. After 7 h, the suspension was filtered and the precipitate washed with 2×10 mL water and dried overnight in the vacuum oven at 40° C. to give a crude yield of 1.26 g as a solid. The mixture of sulfates were separated using preparative LC-MS and both (Id-iib) and (Id-iia) were subjected to purification via trituration, by refluxing in 50 mL MeOH and stirred at room temperature for 32 h. The suspension was filtered, and the precipitate washed with 2×5 mL MeOH, and dried in vacuum oven at 40° C. overnight, then suspended in 50 mL acetonitrile and stirred at room temperature from for 19 h and the precipitate was washed with 2×10 mL acetonitrile and dried in the vacuum oven at 40° C. to give (Id-iib) (4aR,10aR)-6-hydroxy-1-propyl-1,2,3,4,4a,5,10,10a-octahydrobenzo[g]quinolin-7-yl hydrogen sulfate (0.52 g, 1.5 mmol, 30% yield) as a solid and (Id-iia) (4aR,10aR)-7-hydroxy-1-propyl-1,2,3,4,4a,5,10,10a-octahydrobenzo[g]quinolin-6-yl hydrogen sulfate (0.15 g, 0.45 mmol, 9% yield) as a solid.

(Id-iib)

LCMS (method 555) 1.29 min.

$^1$H NMR (600 MHz, DMSO-d$_6$) δ 9.06 (s, 1H), 8.89 (s, 1H), 6.89 (d, J=8.2 Hz, 1H), 6.58 (d, J=8.3 Hz, 1H), 3.52 (d, J=12.1 Hz, 1H), 3.35-3.32 (m, 1H), 3.31-3.22 (m, 2H), 3.10-3.01 (m, 2H), 2.97 (dd, J=17.4, 5.1 Hz, 1H), 2.74 (dd, J=15.6, 11.1 Hz, 1H), 2.18 (dd, J=17.4, 11.6 Hz, 1H), 1.97-1.69 (m, 5H), 1.68-1.56 (m, 1H), 1.35 (qd, J =13.0, 3.8 Hz, 1H), 0.96 (t, J=7.3 Hz, 3H).

(Id-iia)

LCMS (method 555) 1.37 min.

$^1$H NMR (600 MHz, DMSO-d$_6$) δ 9.07 (s, 1H), 8.84 (s, 1H), 6.82 (d, J=8.3 Hz, 1H), 6.70 (d, J=8.3 Hz, 1H), 3.51 (d, J=12.0 Hz, 1H), 3.34-3.30 (m, 1H), 3.26 (bs, 2H), 3.17-2.94 (m, 3H), 2.75-2.67 (m, 1H), 2.35 (dd, J=17.6, 11.9 Hz, 1H), 1.90 (t, J=13.8 Hz, 2H), 1.85-1.69 (m, 3H), 1.67-1.57 (m, 1H), 1.40-1.31 (m, 1H), 0.95 (t, J=7.3 Hz, 3H).

(Id-iiab): (4aR,10aR)-1-propyl-1,2,3,4,4a,5,10,10a-octahydrobenzo[g]quinoline-6,7-diyl bis(hydrogen sulfate) (triethylamine salt)

(Id-iiab)

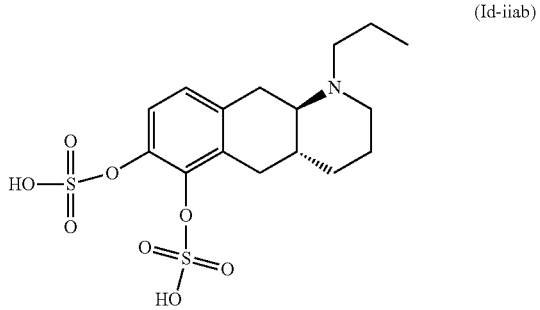 [SMILES: CCCN1CCC[C@@H]2Cc3c(ccc(OS(=O)(=O)O)c3OS(=O)(=O)O)C[C@H]21]

(4aR,10aR)-1-propyl-1,2,3,4,4a,5,10,10a-octahydrobenzo[g]quinoline-6,7-diol hydrochloride (0.500 g, 1.68 mmol) and pyridine sulfur trioxide complex (5.34 g, 33.6 mmol) were suspended in acetonitrile (10 ml) and triethylamine (7.02 ml, 50.4 mmol) was added at room temperature. The suspension was heated to 80° C. and stirred under nitrogen atmosphere for 16.5 h. The mixture was allowed to cool to room temperature and was evaporated onto filter aid (10 g). Purification by column chromatography (eluent: ethyl acetate/triethylamine/MeOH, 75:5:20-45:5:50) afforded an oil (1.51 g). The oil was diluted with MeOH (10 mL+3 drops DMSO) and tert-Butyl methyl ether (MTBE) (2×10 mL) was added by syringe. An oily solid precipitated immediately. The suspension was concentrated and the resulting residue was taken up in MeOH (20 mL) and triethylamine (5 mL) and filtered. MTBE (40 mL) was added to the filtrate over the course of two minutes and a solid gradually precipitated. The precipitate was filtered and dried in the vacuum oven at 35° C. for 15 minutes to yield (4aR,10aR)-1-propyl-1,2,3,4,4a,5,10,10a-octahydrobenzo[g]quinoline-6,7-diyl bis(hydrogen sulfate) as a solid and as a 1:1.3 complex with triethylamine by $^1$-H NMR analysis (0.531 g, 0.957 mmol, 57% yield).

LCMS (method 555) rt=1.00 min.

Due to the instability of the disulfate in acidic conditions, LCMS does not give a good indication of purity.

$^1$H NMR (600 MHz, DMSO-d$_6$) δ 8.93 (s, 1H), 8.80 (s, 1H), 7.40 (d, J=8.5 Hz, 1H), 6.77 (d, J=8.6 Hz, 1H), 3.48 (d, J=11.7 Hz, 1H), 3.37-3.19 (m, 5H), 3.10 (q, J=7.3 Hz, 7.8H, triethylamine), 3.02 (s, 1H), 2.76-2.67 (m, 1H), 2.46 (dd, J =17.7, 12.2 Hz, 1H), 1.85 (d, J=11.3 Hz, 2H), 1.81-1.56 (m, 4H), 1.37-1.26 (m, 1H), 1.17 (t, J=7.3 Hz, 11.7H, triethylamine), 0.95 (t, J=7.3 Hz, 3H).

HRMS (ESI): calcd. m/z for C16H21NO8S22-[M−2H+] 209.5360, found 209.5360

Intermediates for Preparation of (Id-ia), (Id-ib) and (Id-iab)

Intermediates: (4aR,10aR)-1-propyl-7-((triisopropylsilyl)oxy)-1,2,3,4,4a,5,10,10a-octahydrobenzo[g]quinolin-6-ol, and (4aR,10aR)-1-propyl-6-((triisopropylsilyl)oxy)-1,2,3,4,4a,5,10,10a-octahydrobenzo[g]quinolin-7-ol.

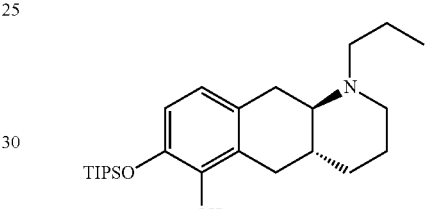

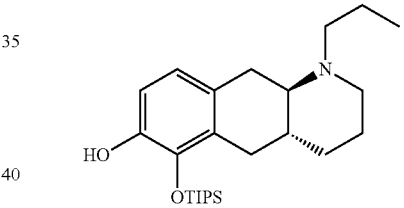

(4aR,10aR)-1-propyl-1,2,3,4,4a,5,10,10a-octahydrobenzo[g]quinoline-6,7-diol, hydrochloride (2.21 g, 7.43 mmol) was suspended in dichloromethane (80 ml) under nitrogen atmosphere at room temperature, N,N-diisopropylethylamine (4.44 g, 6.0 ml, 34.4 mmol) was added followed by triisopropylsilyl chloride (2.73 g, 3.0 ml, 14.16 mmol) and the mixture was stirred at room temperature for 92 h. 10 mL MeOH was added, and the crude mixture was evaporated, co-evaporated twice with dichloromethane/heptane, re-dissolved in dichloromethane, and evaporated directly on filter aid and purified by column chromatography (eluent: n-heptane/ethyl acetate/triethylamine, 100:0:0-35:60:5) affording 3.14 g as a mixture of (4aR,10aR)-1-propyl-7-((triisopropylsilyl)oxy)-1,2,3,4,4a,5,10,10a-octahydrobenzo[g]quinolin-6-ol (3.14 g) and (4aR,10aR)-1-propyl-6-((triisopropylsilyl)oxy)-1,2,3,4,4a,5,10,10a-octahydrobenzo[g]quinolin-7-ol as an oil. NMR (CDCl3) showed>30:1 mixture of silylated isomers Intermediates: tert-butyl ((4aR,10aR)-1-propyl-7-((triisopropylsilyl)oxy)-1,2,3,4,4a,5,10,10a-octahydrobenzo[g]quinolin-6-yl) carbonate [A], and tert-butyl ((4aR,10aR)-1-propyl-6-((triisopropylsilyl)oxy)-1,2,3,4,4a,5,10,10a-octahydrobenzo[g]quinolin-7-yl) carbonate [B].

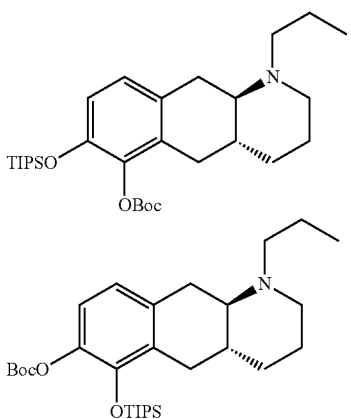

The mixture from the previous step (4aR,10aR)-1-propyl-7-((triisopropylsilyl)oxy)-1,2,3,4,4a,5,10,10a-octahydrobenzo[g]quinolin-6-ol and (4aR,10aR)-1-propyl-6-((triisopropylsilyl)oxy)-1,2,3,4,4a,5,10,10a-octahydrobenzo[g]quinolin-7-ol (2.94 g, 7.04 mmol) was dissolved in dichloromethane (30 ml) under a nitrogen atmosphere and cooled to 0° C. Pyridine (6.00 ml) followed by di-tert-butyl dicarbonate (6.30 g) were added and the reaction mixture was allowed to warm to room temperature over 3-4 h and then stirred at room temperature overnight. 10 mL MeOH was added and the reaction mixture was evaporated, coevaporated with dichloromethane/n-heptane twice, dissolved in dichloromethane, and evaporated on filter aid. Purification by column chromatography (eluent: n-heptane/ethyl acetate/triethylamine, 100:0:0-75:20:5) gave a mixture of tert-butyl ((4aR,10aR)-1-propyl-7-((triisopropylsilypoxy)-1,2,3,4,4a,5,10,10a-octahydrobenzo[g]quinolin-6-yl) carbonate [A] and tert-butyl ((4aR,10aR)-1-propyl-6-((triisopropylsilyl)oxy)-1,2,3,4,4a,5,10,10a-octahydrobenzo[g]quinolin-7-yl) carbonate [B] (3.6 g) as an oil.

NMR (CDCl3) after drying showed a mixture of regioisomers.

Intermediates: (4aR,10aR)-6-((tert-butoxycarbonyl)oxy)-1-propyl-1,2,3,4,4a,5,10,10a-octahydrobenzo[g]quinolin-7-ylacetate, and (4aR,10aR)-7-((tert-butoxycarbonyl)oxy)-1-propyl-1,2,3,4,4a,5,10,10a-octahydrobenzo[g]quinolin-6-ylacetate.

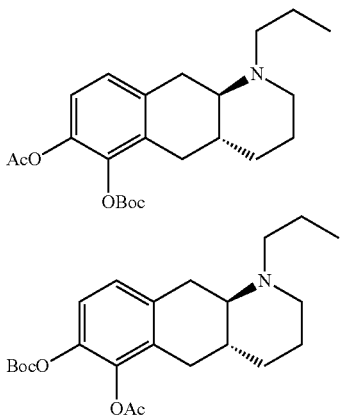

tert-Butyl ((4aR,10aR)-1-propyl-7-((triisopropylsilyl)oxy)-1,2,3,4,4a,5,10,10a-octahydrobenzo[g]quinolin-6-yl) carbonate (3.600 g, 6.95 mmol) (mixture of [A]:[B] from the previous step) was dissolved in THF (150 ml) under nitrogen atmosphere at 0° C., triethylamine trihydrofluoride (2.97 g, 3.00 ml, 18.42 mmol) was added and the mixture was stirred at 0° C. After 3 h at 0° C., pyridine (10.0 ml, 124 mmol) and acetic anhydride (4.33 g, 4.00 ml, 42.4 mmol) were added directly to the reaction mixture at 0° C., and the reaction mixture was allowed to warm to room temperature. After 16 h, 20 mL MeOH was added, and the reaction mixture was evaporated, redissolved in dichloromethane/heptane, and evaporated on filter aid followed by purification by dry column vacuum chromatography affording (4aR,10aR)-6-((tert-butoxycarbonyl)oxy)-1-propyl-1,2,3,4,4a,5,10,10a-octahydrobenzo[g]quinolin-7-yl acetate and (4aR,10aR)-7-((tert-butoxycarbonyl)oxy)-1-propyl-1,2,3,4,4a,5,10,10a-octahydrobenzo[g]quinolin-6-yl acetate as an oil/foam. LCMS (method 550) rt=0.56min, [M+H]+=404 e/z.

Intermediates: (2S,3R,4S,5S,6S)-2-(((4aR,10aR)-7-acetoxy-1-propyl-1,2,3,4,4a,5,10,10a-octahydrobenzo[g]quinolin-6-yl)oxy)-6-(methoxycarbonyl)tetrahydro-2H-pyran-3,4,5-triyl triacetate, and (2S,3R,4S,5S,6S)-2-W4aR,10aR)-6-acetoxy-1-propyl-1,2,3,4,4a,5,10,10a-octahydrobenzo[g]quinolin-7-yl)oxy)-6-(methoxycarbonyl)tetrahydro-2H-pyran-3,4,5-triyl triacetate.

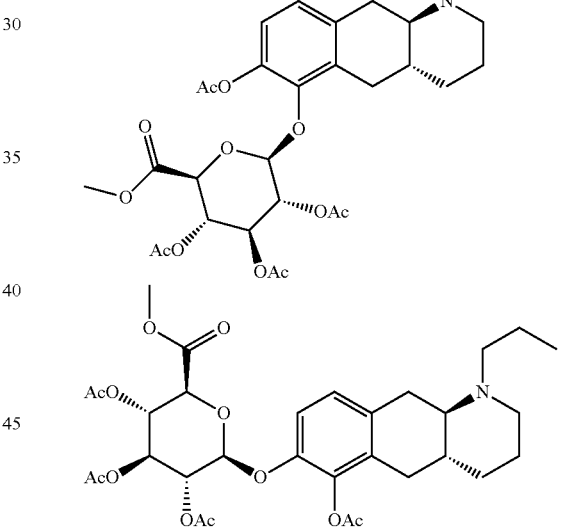

(4aR,10aR)-6-((tert-butoxycarbonyl)oxy)-1-propyl-1,2,3,4,4a,5,10,10a-octahydrobenzo[g]quinolin-7-yl acetate (2.489 g, 6.17 mmol) (mixture of (4aR,10aR)-6-((tert-butoxycarbonyl)oxy)-1-propyl-1,2,3,4,4a,5,10,10a-octahydrobenzo[g]quinolin-7-yl acetate and (4aR,10aR)-7-((tert-butoxycarbonyl)oxy)-1-propyl-1,2,3,4,4a,5,10,10a-octahydrobenzo[g]quinolin-6-yl acetate assumed) was dissolved in dichloromethane (60 ml) under nitrogen atmosphere at room temperature, (2S,3R,4S,5S,6S)-6-(Methoxycarbonyl)tetrahydro-2H-pyran-2,3,4,5-tetrayl tetraacetate (7.529 g, 20.01 mmol) was added followed by the addition of boron trifluoride diethyl etherate (6.72 g, 6.0 ml, 47.3 mmol) and the mixture was stirred at room temperature for 5 days. The mixture was diluted with dichloromethane and MeOH and evaporated on filter aid. Purification by dry column vacuum chromatography to give a mixture of (2S,3R,4S,5S,6S)-2-(((4aR,10aR)-7-acetoxy-1-propyl-1,2,3,4,4a,5,10,10a-octahydrobenzo[g]quinolin-6-yl)oxy)-6-(methoxycarbonyl)tetrahydro-2H-pyran-3,4,5-triyltriacetate and (2S,3R,4S,5S,6S)-2-(((4aR,10aR)-6-acetoxy-1-propyl-1,2,3,4,4a,5,10,10a-octahydrobenzo[g]quinolin-7-yl)oxy)-6-(methoxycarbonyl)tetrahydro-2H-pyran-3,4,5-triyltriacetate (4.37 g) as a foam/solid. LC-MS (method 555) rt=1.94 min, [M+H]⁺=620 e/z.

Intermediate: methyl (2S,3S,4S,5R,6S)-6-[[(4aR,10aR)-1-propyl-6-[(2S,3R,4S,5S,6S)-3,4,5-triacetoxy-6-methoxycarbonyl-tetrahydropyran-2-yl]oxy-3,4,4a,5,10,10a-hexahydro-2H-benzo[g]quinolin-7-yl]oxy]-3,4,5-triacetoxy-tetrahydropyran-2-carboxylate

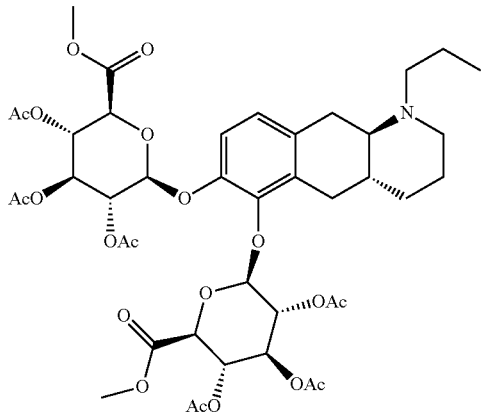 [SMILES: CCCN1CCC[C@@H]2Cc3c(ccc(O[C@@H]4O[C@H](C(=O)OC)[C@@H](OC(C)=O)[C@H](OC(C)=O)[C@H]4OC(C)=O)c3O[C@@H]3O[C@H](C(=O)OC)[C@@H](OC(C)=O)[C@H](OC(C)=O)[C@H]3OC(C)=O)C[C@H]21]

(2S,3S,4S,5R,6R)-2-(methoxycarbonyl)-6-(2,2,2-trichloro-1-iminoethoxy)tetrahydro-2H-pyran-3,4,5-triyltriacetate (1.286 g, 2.69 mmol) and (4aR,10aR)-1-propyl-1,2,3,4,4a,5,10,10a-octahydrobenzo[g]quinoline-6,7-diol, hydrochloride (0.4 g, 1.343 mmol) were dissolved in dichloromethane (5.28 g, 4.00 ml, 62.2 mmol), then boron trifluoride diethyl etherate (0.381 g, 0.340 ml, 2.69 mmol) was added under a nitrogen atmosphere and the mixture stirred for 3 d under nitrogen in a 8 mL vial. Additional (2S,3S,4S,5R,6R)-2-(methoxycarbonyl)-6-(2,2,2-trichloro-1-iminoethoxy)tetrahydro-2H-pyran-3,4,5-triyl triacetate (1.286 g, 2.69 mmol) and boron trifluoride diethyl etherate (0.381 g, 0.340 ml, 2.69 mmol) were added and the mixture was stirred for 4 h, then the mixture was poured into saturated aqueous NaHCO₃ (30 mL), then extracted with dichloromethane (2×20 mL) and the combined organic phases were dried (Na₂SO₄), filtered, and evaporated into dryness in vacuo. The crude foam was suspended in heptane/ethyl acdetate (1:1) and stirred overnight. Subsequently, HCl in ether (0.672 ml, 1.343 mmol, 2 molar) was added and the mixture stirred for 1 h and was evaporated to dryness in vacuo and MTBE (40 mL) was added and the mixture was heated to reflux and allowed to cool to room temperature, then the mixture was filtered and the solid was dried in the vacuum oven for 1day at 40° C. affording methyl (2S,3S,4S,5R,6S)-6-[[(4aR,10aR)-1-propyl-6-[(2S,3R,4S,5S,6S)-3,4,5-triacetoxy-6-methoxycarbonyl-tetrahydropyran-2-yl]oxy-3,4,4a,5,10,10a-hexahydro-2H-benzo[g]quinolin-7-yl]oxy]-3,4,5-triacetoxy-tetrahydropyran-2-carboxylate, Hydrochloride (1.0854 g, 1.167 mmol, 87% yield).
LC-MS method 550 rt=0.63 min, [M+H]⁺=895.7 e/z.
(Id-ib): (2S,3S,4S,5R,6S)-3,4,5-trihydroxy-6-(((4aR,10aR)-6-hydroxy-1-propyl-1,2,3,4,4a,5,10,10a-octahydrobenzo[g]quinolin-7-yl)oxy)tetrahydro-2H-pyran-2-carboxylic acid, and (Id-ia): (2S,3S,4S,5R,6S)-3,4,5-trihydroxy-6-(((4aR,10aR)-7-hydroxy-1-propyl-1,2,3,4,4a,5,10,10a-octahydrobenzo[g]quinolin-6-yl)oxy)tetrahydro-2H-pyran-2-carboxylic acid.

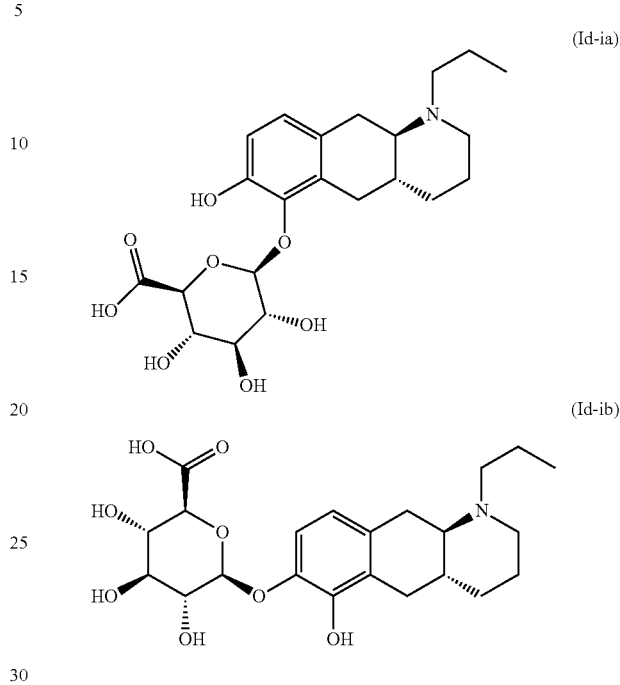

A mixture of (2S,3R,4S,5S,6S)-2-(((4aR,10aR)-7-acetoxy-1-propyl-1,2,3,4,4a,5,10,10a-octahydrobenzo[g]quinolin-6-yl)oxy)-6-(methoxycarbonyl)tetrahydro-2H-pyran-3,4,5-triyl triacetate and (2S,3R,4S,5S,6S)-2-W4aR,10aR)-6-acetoxy-1-propyl-1,2,3,4,4a,5,10,10a-octahydrobenzo[g]quinolin-7-yl)oxy)-6-(methoxycarbonyl)tetrahydro-2H-pyran-3,4,5-triyl triacetate (3.82 g, 6.17 mmol) was dissolved in MeOH (100 ml) and water (20 ml), cooled to 0° C., potassium cyanide (7.295 g, 112 mmol) was added and the suspension was allowed to slowly warm to room temperature for 17.5 h. The crude mixture was evaporated on filter aid and dried. The crude mixture was purified by silica gel column chromatography (eluent: ethyl acetate/MeOH/water 100:0:0-0:50:50), affording a 5-6:1 ratio of (Id-ib) and (Id-ia). The mixture was separated by preparative LCMS. Collected Peak 1 fractions containing (Id-ib) were pooled, evaporated, and combined with another batch of 186 mg (Id-ib)-TFA, which had been prepared in a similar manner, using MeOH, evaporated, and dried to give a solid. (Id-ib) was re-suspended in 10 mL EtOH, and 100 mL MTBE was added, and the resulting suspension was stirred at room temperature for 8 h, the suspension was filtered and the precipitate washed with 2×10 mL MTBE and dried in a vacuum oven overnight to afford (Id-ib) 1.601 g, as a solid corresponding to (2S,3S,4S,5R,6S)-3,4,5-trihydroxy-6-(((4aR,10aR)-6-hydroxy-1-propyl-1,2,3,4,4a,5,10,10a-octahydrobenzo[g]quinolin-7-yl)oxy)tetrahydro-2H-pyran-2-carboxylic acid.
Collected Peak 2 fractions containing (Id-ia) were pooled, evaporated, transferred to smaller flask with MeOH, evaporated, redissolved in ca. 12 mL MeOH, and repurified by preparative LCMS, and evaporated to give a foam/solid. Appropriate fractions were pooled, evaporated, transferred with MeOH to a smaller flask, and evaporated and combined with another batch of 40.7 mg (Id-ia), which had been prepared in a similar manner. The combined batch was dissolved in 2.5 mL EtOH, 25 mL MTBE was added, and the suspension was stirred at room temperature. After 8 h, the suspension was filtered and the precipitate washed with 2×2.5 mL MTBE and dried in the vacuum oven overnight to give 362.2 mg of (Id-ia) as a solid. (Id-ia) was suspended in ca. 10 mL EtOH, 50 mL MTBE was added, and the suspension was stirred at room temperature and filtered after 19 h and the precipitate was washed with 2×10 mL MTBE, and dried in the vacuum oven at 40° C. to give (2S,3S,4S, 5R,6S)-3,4,5-trihydroxy-6-(((4aR,10aR)-7-hydroxy-1-propyl-1,2,3,4,4a,5,10,10a-octahydrobenzo[g]quinolin-6-yl) oxy)tetrahydro-2H-pyran-2-carboxylic acid (Id-ia) 0.279 g as a solid.

(Id-ib)
LCMS (method 551) rt=0.37 min.
$^1$H NMR (600 MHz, Methanol-$d_4$) δ 7.02 (d, J=8.4 Hz, 1H), 6.65 (d, J=8.4 Hz, 1H), 4.73 (d, J=7.7 Hz, 1H), 3.89 (d, J=9.7 Hz, 1H), 3.68-3.58 (m, 2H), 3.54 (dd, J=9.3, 7.7 Hz, 1H), 3.49 (t, J=9.1 Hz, 1H), 3.47-3.36 (m, 2H), 3.30 (dt, J=11.2, 5.6 Hz, 1H), 3.21-3.11 (m, 3H), 2.85 (dd, J=15.4, 11.3 Hz, 1H), 2.35 (dd, J=17.6, 11.5 Hz, 1H), 2.12-2.02 (m, 2H), 2.02-1.84 (m, 3H), 1.81-1.71 (m, 1H), 1.49 (qd, J=13.0, 3.7 Hz, 1H), 1.09 (t, J=7.3 Hz, 3H).

(Id-ia)
LCMS (method 551) rt=0.39 min.
$^1$H NMR (600 MHz, Methanol-$d_4$) δ 6.87 (d, J=8.3 Hz, 1H), 6.74 (d, J=8.4 Hz, 1H), 4.62 (d, J=7.9 Hz, 1H), 3.75 (dd, J=17.7, 4.9 Hz, 1H), 3.66-3.62 (m, 2H), 3.61-3.51 (m, 2H), 3.50-3.35 (m, 3H), 3.31-3.22 (m, 1H), 3.14 (qd, J=12.7, 4.0 Hz, 2H), 2.83 (dd, J=15.2, 11.3 Hz, 1H), 2.37 (dd, J=17.7, 11.7 Hz, 1H), 2.12 (d, J=13.4 Hz, 1H), 2.08-2.00 (m, 1H), 1.98-1.83 (m, 3H), 1.81-1.71 (m, 1H), 1.44 (qd, J=13.2, 3.9 Hz, 1H), 1.09 (t, J=7.3 Hz, 3H).

(Id-iab): (2S,2'S,3S,3'S,4S,4'S,5R,5'R,6S,6'S)-6,6'-(((4aR,10aR)-1-propyl-1,2,3,4,4a,5,10,10a-octahydrobenzo[g]quinoline-6,7-diyl)bis(oxy))bis(3,4,5-trihydroxytetra hydro-2H-pyra n-2-carboxylic acid).

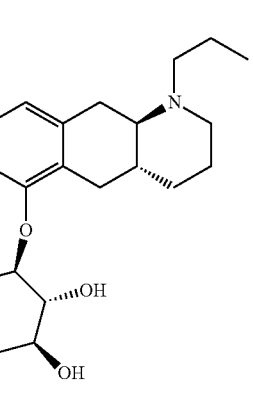

(Id-iab)

Synthesis A.
(1S,4aR,10aR)-1-propyl-6,7-bis(((2S,3R,4S,5S,6S)-3,4,5-triacetoxy-6-(methoxycarbonyl)tetrahydro-2H-pyran-2-yl) oxy)-1,2,3,4,4a,5,10,10a-octahydrobenzo[g]quinoline (0.25 g, 0.269 mmol) was dissolved in water (1.209 g, 1.209 ml, 67.1 mmol) and MeOH (3.83 g, 4.84 ml, 120 mmol) and KOH (0.393 g, 0.270 ml, 3.22 mmol, 46%) were added and stirred overnight at room temperature in a sealed vial. A precipitate had formed overnight, which was isolated via filtration. The solid was washed with MeOH (1.5 mL) affording (2S,2'S,3S,3'S,4'S,4'S,5R,5'R,6S,6'S)-6,6'-(((4aR, 10aR)-1-propyl-1,2,3,4,4a,5,10,10a-octahydrobenzo[g]quinoline-6,7-diyl)bis(oxy))bis(3,4,5-trihydroxytetrahydro-2H-pyran-2-carboxylic acid), 2Potassium (0.096 g, 0.139 mmol, 51.6% yield)

LC-MS method 551 rt 0.31 min, [M+H]$^+$=614.2 e/z.

Synthesis B.
(1S,4aR,10aR)-1-propyl-6,7-bis(((2S,3R,4S,5S,6S)-3,4,5-triacetoxy-6-(methoxycarbonyl)tetrahydro-2H-pyran-2-yl) oxy)-1,2,3,4,4a,5,10,10a-octahydrobenzo[g]quinoline (0.2585 g, 0.278 mmol) was dissolved in WATER (1.250 g, 1.25 ml, 69.4 mmol) and MeOH (3.96 g, 5 ml, 124 mmol) and KCN (0.344 g, 5.28 mmol) were added and stirred overnight at room temperature in a sealed vial. A precipitate had formed overnight, which was isolated via filtration. The solid was washed with MeOH (1.5 mL) affording (2S,2'S, 3S,3'S,4S,4'S,5R,5'R,6S,6TS)-6,6'-(((4aR,10aR)-1-propyl-1,2,3,4,4a,5,10,10a-octahydrobenzo[g]quinoline-6,7-diyl) bis(oxy))bis(3,4,5-trihydroxytetra hydro-2H-pyran-2-carboxylic acid), 2Potassium (0.0963 g, 0.139 mmol, 50.1% yield)

LC-MS method 551 rt=0.34 min, [M+H]$^+$=614.6 e/z.

1H NMR (600 MHz, DMSO-d6) δ 7.09 (d, J=8.5 Hz, 1H), 6.84 (d, J=8.5 Hz, 1H), 4.91-4.79 (m, 1H), 4.78-4.66 (m, 1H), 3.93 (bs, 22H (OH/water)), 3.42 (d, J=9.8 Hz, 1H), 3.37-3.21 (m, 7H), 3.19 (s, 1H), 3.11 (dd, J=16.2, 4.9 Hz, 1H), 2.90 (d, J=11.0 Hz, 1H), 2.67 (ddd, J=12.9, 10.7, 5.6 Hz, 1H), 2.49 (dd, J=15.9, 10.9 Hz, 1H), 2.39-2.27 (m, 1H), 2.15 (dt, J=17.5, 11.5 Hz, 2H), 2.05 (td, J=10.4, 4.9 Hz, 1H), 1.86 (d, J=11.7 Hz, 1H), 1.67-1.38 (m, 5H), 1.03 (qd, J=12.3, 5.1 Hz, 1H), 0.85 (t, J=7.3 Hz, 3H).

Further Compounds Encompassed by the Scope of the Invention

The following two compounds are also encompassed by the scope of the invention:

(Id-iaiib): (2S,3S,4S,5R,6S)-3,4,5-trihydroxy-6-(((4aR, 10aR)-1-propyl-7-sulfo-1,2,3,4,4a,5,10,10a-octahydrobenzo[g]quinolin-6-yl)oxy)tetrahydro-2H-pyran-2-carboxylic acid, and (Id-iiaiib): (2S,3S,4S,5R,6S)-3,4,5-trihydroxy-6-(((4aR, 10aR)-1-propyl-6-sulfo-1,2,3,4,4a,5,10,10a-octahydrobenzo[g]quinolin-7-yl)oxy)tetrahydro-2H-pyran-2-carboxylic acid.

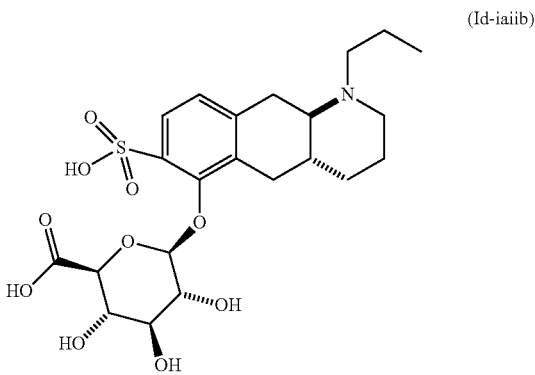

(Id-iaiib)

-continued (Id-iiaib)

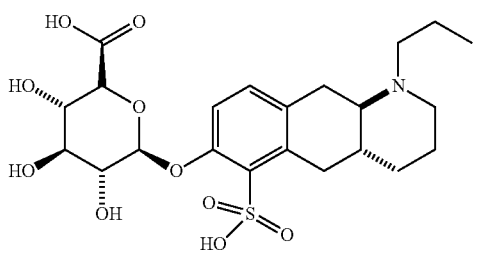

Preparation of Apomorphine Conjugates for PK Comparison (R)-11-hydroxy-6-methyl-5,6,6a,7-tetrahydro-4H-dibenzo[de,g]quinolin-10-yl hydrogen sulfate

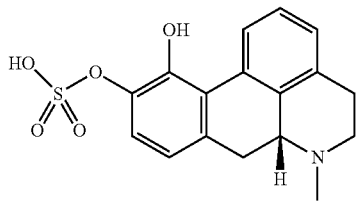 [SMILES: CN1CCc2cccc3c2[C@H]1Cc1ccc(OS(=O)(=O)O)c(O)c1-3]

1.0 g (3.19 mmol, 1.0 eq) Apomorphine hydrochloride hemihydrate was suspended in 3.3 mL pyridine under Argon atmosphere at room temperature. 1.7 g (10.68 mmol, 3.34 eq.). Sulfur trioxide-pyridine complex was added to this suspension and it was stirred at 40° C. temperature for 17 hours and purified by preparative HPLC.
The major isomer (R)-11-hydroxy-6-methyl-5,6,6a,7-tetrahydro-4H-dibenzo[de,g]quinolin-10-yl hydrogen sulfate was isolated (78 mg), 98.8% UV Purity.
LC-MS method 111 rt=5.18 min, [M+H]$^+$=348.1 e/z.
1H NMR (500 MHz, DMSO-d6) δ 9.91 (br, 1H), 9.30 (s, 1H), 8.27 (d, J=5.0 Hz, 1H), 7.39 (m, 1H), 7.20 (d, J=5.0 Hz, 1H), 7.10 (d, J=5.0Hz, 1H), 6.84 (d, J=5.0 Hz, 1H), 4.42 (bs, 1H), 3.77 (bs, 1H), 3.45 (d, J=10.0 Hz, 2H), 3.25-3.21 (m, 1 h), 3.20-3.10 (m, 4 h), 2.71 (t, J=10.0 Hz, 1H).
(R)-10-hydroxy-6-methyl-5,6,6a,7-tetrahydro-4H-dibenzo[de,g]quinolin-11-yl hydrogen sulfate:

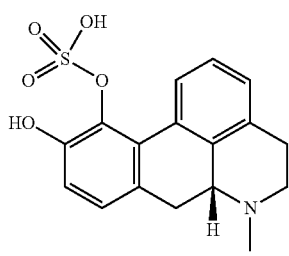 [SMILES: CN1CCc2cccc3c2[C@H]1Cc1ccc(O)c(OS(=O)(=O)O)c1-3]

The same method was used as for (R)-11-hydroxy-6-methyl-5,6,6a,7-tetrahydro-4H-dibenzo[de,g]quinolin-10-yl hydrogen sulfate only slight changes were made to get minor component: the reaction time was reduced to 3 hours and the sulfur trioxide-pyridine was added in three portions. (three batches were performed starting from 850 mg, and twice from 500 mg). The reaction mixtures were pooled and purified by preparative HPLC affording 50 mg of the minor isomer (R)-10-hydroxy-6-methyl-5,6,6a,7-tetrahydro-4H-dibenzo[de,g]quinolin-11-yl hydrogen sulfate.
LC-MS method 222 rt=4.99 min, [M+H]$^+$=348.1 e/z.
1H NMR (500 MHz, DMSO-d6) δ 10.00 (br, 1H), 9.30 (s, 1H), 8.26 (bs, 1H), 7.23 (bs, 1H), 7.11 (bs, 1H), 7.01 (d, J=10.0 Hz, 1H), 6.78 (d, J=10.0 Hz, 1H), 3.50-2.20 (m, 7 h).
Intermediate: (2S,3R,4S,5S,6S)-2-MR)-11-hydroxy-6-methyl-5,6,6a,7-tetrahydro-4H-dibenzo[de,g]quinolin-ß-yl)oxy)-6-(methoxycarbonyl)tetrahydro-2H-pyran-3,4,5-triyl triacetate

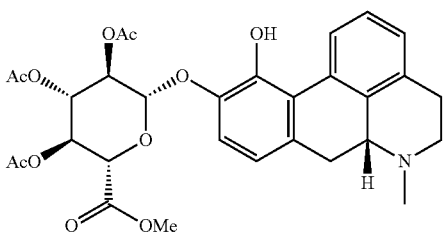 [SMILES: COC(=O)[C@H]1O[C@@H](Oc2ccc3c(c2O)-c2cccc4c2[C@@H](C3)N(C)CC4)[C@H](OC(C)=O)[C@@H](OC(C)=O)[C@@H]1OC(C)=O]

480 mg (1.796 mmol) Apomorphine (free base) and 4.72 g (12.54 mmol, 7.0 eq.) 1,2,3,4-tetra-o-acetyl-ß-D-glucopyranuronate was dissolved in 40 mL dichloromethane under an argon atmosphere at room temperature. The starting materials dissolved in 10 minutes giving a blue solution. To this solution 3.0 mL (3.45 g, 13.5 eq.) boron trifluoride ethyl etherate was added under Ar atmosphere and it was stirred at room temperature for 2 hours. The reaction was poured to 80 mL saturated sodium bicarbonate solution, stirred for 10 minutes, then separated. The water phase was extracted with CH$_2$Cl$_2$ (3×40 mL). The combined organic phases were washed with saturated sodium bicarbonate solution (1×40 mL) and brine (1×40 mL), dried over sodium sulphate, filtered and evaporated, 4.5 g solid was obtained (theoretical yield ~1.0 g). The crude product was purified with flash chromatography using CH$_2$Cl$_2$:MeOH=96:4. After purification 190 mg (2S,3R,4S,5S,6S)-2-(((R)-11-hydroxy-6-methyl-5,6,6a,7-tetrahydro-4H-dibenzo[de,g]quinolin-10-yl)oxy)-6-(methoxycarbonyl)tetrahydro-2H-pyran-3,4,5-triyltriacetate was obtained.
(2S,3S,4S,5R,6S)-3,4,5-trihydroxy-6-(UR)-11-hydroxy-6-methyl-5,6,6a,7-tetrahydro-4H-dibenzo[de,g]quinolin-10-yl)oxy)tetrahydro-2H-pyran-2-carboxylic acid

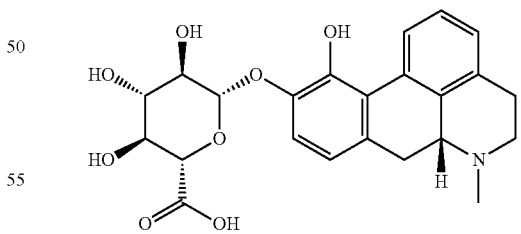

250 mg (0.432 mmol) (2S,3R,4S,5S,6S)-2-(((R)-11-hydroxy-6-methyl-5,6,6a,7-tetrahydro-4H-dibenzo[de,g]quinolin-10-yl)oxy)-6-(methoxycarbonyl)tetrahydro-2H-pyran-3,4,5-triyl triacetate was dissolved in a mixture of 6.1 mL MeOH and 1.2 mL water, and cooled to 0° C. At that temperature 526 mg (8.07 mmol 18.7 eq) KCN was added. The reaction mixture was stirred and let warm up to room temperature and stirred for additional 2 hours. The reaction was filtered and purified directly on preparatory HPLC in water-acetonitrile-0.1% TFA eluent. From the collected fractions the acetonitrile was evaporated at room temperature in vacuum and aqueous residue was lyophilized affording 133 mg of the TFA salt of (2S,3S,4S,5R,6S)-3,4,5-trihydroxy-6-(((R)-11-hydroxy-6-methyl-5,6,6a,7-tetrahydro-4H-dibenzo[de,g]quinolin-10-yl)oxy)tetrahydro-2H-pyran-2-carboxylic acidas a powder. Its structure was verified by LCMS and NMR.

LC-MS method 111 rt=4.30 min, [M+H]$^+$=444.2 e/z.
1H NMR (500 MHz, DMSO-d6) δ 12.84 (br, 1H), 10.00 (bs, 1H), 8.87 (s, 1H), 8.29 (d, J=10.0 Hz, 1H), 7.40 (m, 1H), 7.21 (d, J=5.0 Hz, 1H), 7.02 (d, J=10.0 Hz, 1H), 6.83 (d, J=5.0 Hz, 1H), 5.77 (s, 1H), 5.45-5.20 (m, 2H), 4.84 (d, J=5.0 Hz, 1H), 4.34 (bs, 1H), 3.92 (d, J=10.0 Hz, 1H), 3.76 (bs, 1 h), 3.55-3.00 (m, 11H, OH/water), 2.75-3.30 (m, 4H).

In Vitro and In Vivo Characterization of Compounds of the Invention

EXAMPLE 1a

Conversion of the Compounds of the Invention in Rat and Human Hepatocytes

The compounds (Id-ia), (Id-ib), (Id-iia), (Id-iib), (Id-iab) and (Id-iiab) were incubated separately at 1 μg/mL with hepatocytes from human or rat suspended in DMEM (Dulbecco's Modified Eagle Medium) with HEPES (4-(2-hydroxyethyl)-1-piperazineethanesulfonic acid) at pH 7.4. The cell concentration at incubation was 1×10$^6$ viable cells/mL. The incubations were performed in glass tubes at 37° C. with a total incubation volume of 3.5 mL and with duplicate incubations for each test item. The 3.5 mL of hepatocyte suspension was equilibrated for 10 minutes in a water bath set to 37° C. where after the incubations were initiated by adding 3.5 μL of a stock solution of the test item in DMSO (Dimethyl sulfoxide) and gently inverting the tubes. The final solvent concentration in the incubations was 0.1% DMSO. Samples of 600 μL were withdrawn from the incubations at the pre-determined time points of 0.25, 5, 15, 30 and 60 minutes after ensuring homogeneity of hepatocyte suspensions. The withdrawn volume was added to 1 mL Nunc cryo tubes on wet ice containing 60 μL of ice cold ascorbic acid (100 mg/mL) and 30 μL of ice cold 100 mM saccharic acid 1.4-lactone in 0.5 M citric acid. The tubes were mixed and 35 μL of a solution of ice cold 20% formic acid was added. The tubes were mixed thoroughly and stored at −80° C. awaiting analysis. Analysis method and Instrumentation used for analysis of (I) from dosing (Id-ia), (Id-ib), (Id-iia) and (Id-iib), were the one described in Examples 4 and 5 below in the section "Instrumentation used for analysis of compound (I) from dosing of compounds (Ic), (Id-ia), (Id-ib), (Id-iia), (Id-iib), (Id-iab) and (Id-iiab)."

Analysis method and Instrumentation used for analysis of (I) from dosing (Id-iab) and (Id-iiab) consisted of mixing equal aliquots of the samples and precipitation solution (acetonitrile (MeCN) with 10% methanol (MeOH) and 1% formic acid), followed by centrifugation at 4° C. at 16000 g for 10 minutes. Supernatants were collected and analysed by LC-MS/MS. Mass spectrometer: Waters Acquity-Waters Xevo TQ-MS. Analytical column: Acquity UPLC HSS T3, 100×2.1 mm, 1.8 μm. Mobile phase A: 0.2% formic acid in water. Mobile phase B: 0.2% formic acid in acetonitrile. Gradient run from 95/5% to 60/40 in 5 min. Flow rate 0.3 mL/min. MRM monitoring of (I) in the study samples and in the analytical standards.

FIG. 7 indicates a time dependent conversion to compound (I) from (Id-ia), (Id-ib), (Id-iia), (Id-iib) and (Id-iab) in both rat and human hepatocytes. For (Id-iiab) formation of compound (I) could not be detected at the given test conditions.

EXAMPLE 1b

Conversion of the Compounds of the Invention in Fresh Rat and Human Blood

Conversion of (Id-ia), (Id-ib), (Id-iia) and (Id-iib) in human blood (average of 3 donors) and rat blood (average of 45 donors) to (I) was shown in fresh blood at 37° C. spiked with 1 μg/mL of (Id-ia), (Id-ib), (Id-iia) and (Id-iib) separately, (I) was measured at 0, 5, 15, 30 and 60 minutes in isolated plasma. Analysis method and Instrumentation as described in Examples 4 and 5 below in the section "Instrumentation used for analysis of compound (I) from dosing of compounds (Ic), (Id-ia), (Id-ib), (Id-iia), (Id-iib), (Id-iab) and (Id-iiab)."

FIG. 8 indicates a time dependent conversion to compound (I) from (Id-ia), (Id-ib), (Id-iia) and (Id-iib) in both rat and human blood.

EXAMPLE 2

Dopamine Agonist Activity

Dopamine D1 Receptor Agonism

Dopamine D1 receptor agonism was measured using a HTRF cAMP from CisBio using the protocol developed by HD Biosciences (China). Briefly, the assay is a homogeneous time resolved-fluorescence resonance energy transfer (HTRF) assay that measures production of cAMP by cells in a competitive immunoassay between native cAMP produced by cells and cAMP-labeled with XL-665. A cryptate-labeled anti-cAMP antibody visualizes the tracer. The assay was performed in accordance with instructions from manufacturer.

Test compounds were added to wells of microplates (384 format). HEK-293 cells expressing the human D1 receptor were plated at 1000 cells/well and incubated 30 min at room temperature. cAMP-d2 tracer was added to wells and followed by addition of Anti-cAMP antibody-cryptate preparation and incubated for 1 h at room temperature in dark. HTRF cAMP was measured by excitation of the donor with 337 nm laser (the "TRF light unit") and subsequent (delay time 100 microseconds) measurement of cryptate and d2 emission at 615 nm and 665 nm over a time window of 200 microseconds with a 2000 microseconds time window between repeats/100 flashes). HRTF measurements were performed on an Envision microplate reader (PerkinElmer). The HTRF signal was calculated as the emission-ratio at 665 nm over 615 nm. The HTRF ratio readout for test compounds was normalized to 0% and 100% stimulation using control wells with DMSO-solvent or 30 uM dopamine. Test compound potency (EC50) was estimated by nonlinear regression using the sigmoidal dose-response (variable slope) using Xlfit 4 (IDBS, Guildford, Surrey, UK, model 205).

$$y=(A+((B-A)/(1+((C/x)^D))))$$

where y is the normalized HTRF ratio measurement for a given concentration of test compound, x is the concentration of test compound, A is the estimated efficacy at infinite compound dilution, and B is the maximal efficacy. C is the EC50 value and D is the Hill slope coefficient. EC50 estimates were obtained from an independent experiment and the logarithmic average was calculated.

Dopamine D2 Receptor Agonism

Dopamine D2 receptor agonism was measured using a calcium mobilization assay protocol developed by HD Biosciences (China). Briefly, HEK293/G15 cells expressing human D2 receptor were plated at a density of 15000 cells/well in clear-bottomed, Matrigel-coated 384-well plates and grown for 24 hrs at 37° C. in the presence of 5% $CO_2$. The cells were incubated with calcium-sensitive fluorescent dye, Fluo8, for 60-90 minutes at 37° C. in the dark. Test compounds were prepared at 3-fold concentrated solution in 1×HBSS buffer with $Ca^{2+}$ and $Mg^{2+}$. Calcium Flux signal was immediately recorded after compounds were added from compound plate to cell plate at FLIPR (Molecular Devices). The fluorescence data were normalized to yield responses for no stimulation (buffer) and full stimulation (1 µM of dopamine) of 0% and 100% stimulation, respectively. Test compound potency (EC50) was estimated by nonlinear regression using the sigmoidal dose-response (variable slope) using XIfit 4 (IDBS, Guildford, Surrey, UK, model 205).

$y=(A+((B-A)/(1+((C/x)^D))))$ where y is the normalized ratio measurement for a given concentration of test compound, x is the concentration of test compound, A is the estimated efficacy at infinite compound dilution, and B is the maximal efficacy. C is the EC50 value and D is the Hill slope coefficient. EC50 estimates were obtained from independent experiment and the logarithmic average was calculated.

EXAMPLE 3

5-HT2B Agonist Activity and Binding Assay

5-HT2B Agonist Activity Assay

Evaluation of the agonist activity of compounds (I), (Ia) and (Ib) at the human 5-HT2B receptor was performed by Eurofins/Cerep (France) measuring the compound effects on inositol monophosphate (IP1) production using the HTRF detection method. Briefly, the human 5-HT2B receptor was expressed in transfected CHO cells. The cells were suspended in a buffer containing 10 mM Hepes/NaOH (pH 7.4), 4.2 mM KCl, 146 mM NaCl, 1 mM $CaCl_2$, 0.5 mM MgCl2, 5.5 mM glucose and 50 mM LiCl, then distributed in microplates at a density of 4100 cells/well and incubated for 30 min at 37° C. in the presence of buffer (basal control), test compound or reference agonist. For stimulated control measurement, separate assay wells contained 1 µM 5-HT. Following incubation, the cells were lysed and the fluorescence acceptor (fluorophen D2-labeled IP1) and fluorescence donor (anti-IP1 antibody labeled with europium cryptate) were added. After 60 min at room temperature, the fluorescence transfer was measured at lambda(Ex) 337 nm and lambda(Em) 620 and 665 nm using a microplate reader (Rubystar, BMG). The IP1 concentration was determined by dividing the signal measured at 665 nm by that measured at 620 nm (ratio). The results were expressed as a percent of the control response to 1 µM 5-HT. The standard reference agonist was 5-HT, which was tested in each experiment at several concentrations to generate a concentration-response curve from which its EC50 value is calculated as described above for dopamine functional assays.

5-HT2B Binding Assay

Evaluation of the affinity of compounds (Id-ia), (Id-ib), (Id-iia), (Id-iib) and (Id-iab) for the human 5-HT2B receptor was determined in a radioligand binding assay at Eurofins/Cerep (France). Membrane homogenates prepared from CHO cells expressing the human 5HT2B receptor were incubated for 60 min at room temperature with 0.2 nM [125I](±)DOI (1-(4-iodo-2,5-dimethoxyphenyl)propan-2-amine) in the absence or presence of the test compound in a buffer containing 50 mM Tris-HCl (pH 7.4), 5 mM $MgCl_2$, 10 µM pargyline and 0.1% ascorbic acid. Nonspecific binding is determined in the presence of 1 µM (±)DOI. Following incubation, the samples were filtered rapidly under vacuum through glass fiber filters (GF/B, Packard) presoaked with 0.3% polyethyleneimine (PEI) and rinsed several times with ice-cold 50 mM Tris-HCl using a 96-sample cell harvester (Unifilter, Packard). The filters were dried and counted for radioactivity in a scintillation counter (Topcount, Packard) using a scintillation cocktail (Microscint 0, Packard). The results are expressed as a percent inhibition of the control radioligand specific binding. The standard reference compound was (±)DOI, which was tested in each experiment at several concentrations to obtain a competition curve from which its $IC_{50}$ is calculated.

TABLE 2

In vitro activities for the compounds of the invention obtained according to Examples 2 and 3.

|  | Compound | D1 $EC_{50}$ (nM)/Emax | D2 $EC_{50}$ (nM)/Emax | 5-HT2B $EC_{50}$ (nM)/Emax |
|---|---|---|---|---|
| Parent compound | (I) | 3.3/99% | 1.3/91% | 2900 nM/50% |
| Prior art prodrugs | (Ia) | >1000 | >1000 | >6000 nM, 58% @30 uM |
|  | (Ib) | >1000 | 46 nM/100% | 3.8 nM/79% |
|  | (Ic) | nd | nd | −5% @10 µM |
| Compounds of the invention | (Id-ia) | 2700/98% | 1100/92% | −25% @10 µM* |
|  | (Id-ib) | 1800/94% | 1300/100% | −39% @10 µM* |
|  | (Id-iia) | >30000/49% | >30000/48% | 6% @10 µM* |
|  | (Id-ib) | >30000/42% | >30000/54% | 25% @10 µM* |
|  | (Id-iab) | nd | nd | 17% @10 µM |
|  | (Id-iiab) | nd | nd | nd |

*indicate binding affinity (% inhibition of control, specific binding at concentration indicated)
nd: not determined

EXAMPLE 4

PK Experiments in Rats

For all the experiments, blood samples of approximately 0.68 mL were drawn from the tail or sublingual vein and put into K3EDTA tubes that had been pre-cooled and prepared with stabilizing solution consisting of 80 μL ascorbic acid and 40 μL 100 mM D-saccharic acid 1,4 lactone in water. The tubes were inverted gently 6-8 times to ensure thorough mixing and then placed in wet ice. The collecting tube was placed in wet ice for up to 30 minutes until centrifugation. Once removed from the wet ice the centrifugation was initiated immediately. Immediately after end of centrifugation the samples were returned to wet ice. Three sub-samples of 130 μL plasma were transferred to each of three appropriately labelled cryo tubes containing 6.5 μL pre-cooled formic acid (20%) (the tubes were pre-spiked and stored refrigerated prior to use). The tube lid was immediately replaced and the plasma solution was thoroughly mixed by inverting gently 6-8 times. The samples were stored frozen at nominally −70° C. within 60 minutes after sampling. Centrifugation conditions at 3000 G for 10 minutes at 4° C. Plasma was placed on water-ice following collection. Final storage at approximately −70° C.

Plasma samples were analyzed by solid phase extraction or direct protein precipitation followed by UPLC-MS/MS. MS detection using electrospray in the positive ion mode with monitoring of specific mass-to-charge transitions for compound (I) using internal standards for correcting the response. The concentration-time data was analyzed, using standard software using appropriate noncompartmental techniques to obtain estimates of the derived PK parameters.

Instrumentation Used for Analysis of Compound (I) from Dosing Compound (Ia):

Mass spectrometer (LC-MS/MS) Waters Acquity-Sciex API 5000. Analytical column Waters BEH UPLC Phenyl 100×2.1 mm column, 1.7 μm particle size. Mobile phase A: 20 mM ammonium formate (aq)+0.5% formic acid. Mobile phase B: Acetonitrile. Gradient run from 95/5% to 2/98 in 6.1 min. Flow rate 0.5 mL/min. MRM monitoring (multiple reaction monitoring) of test item and the added analytical standards Dosing and blood sampling: Han Wistar rats were supplied by Charles River Laboratories, Sulzfeld, Germany. An artificial, automatically controlled, light and dark cycle of 12 hours was maintained. The rats received a standard laboratory diet from Brogaarden (Altromin 1324 pellets). The rats had unrestricted access to the diet. During the study (a 4-week toxicity study) the rats received once daily doses of (Ia) orally by gavage. From rats given 300 μg/kg (Ia), blood samples) from 3 male satellite animals were collected on the following time points at Day 29: 0.5, 1, 2, 4, 6, 8, 12 and 24 hours after dosing.

Instrumentation Used for Analysis of Compound (I) from Dosing of Compound (Ib):

Mass spectrometer (LC-MS/MS) Waters Acquity -Sciex API 5000. Analytical column Waters BEH UPLC Phenyl 100×2.1 mm column, 1.7 μm particle size. Mobile phase A: 20 mM ammonium formate (aq)+0.5% formic acid. Mobile phase B: Acetonitrile. Gradient run from 95/5% to 2/98 in 6.1 min. Flow rate 0.5 mL/min. MRM monitoring of test item and the added analytical standards.

Dosing and blood sampling: Han Wistar rats were supplied by Charles River Laboratories, UK. An artificial, automatically controlled, light and dark cycle of 12 hours was maintained. The rats received a standard laboratory diet (Teklad 2014C Diet.). The rats had unrestricted access to the diet. During the study (a 26-week toxicity study) the rats received once daily doses of (Ib) orally by gavage. From rats given 300 μg/kg (Ib), blood samples from 3 male satellite animals were collected on the following time points at day 182: 0.5, 1, 2, 4, 8 and 24 hours after dosing.

Instrumentation Used for Analysis of Compound (I) from Dosing of Compounds (Ic), (Id-ia), (Id-ib), (Id-iia), (Id-iib), (Id-iab) and (Id-iiab).

Mass spectrometer (LC-MS/MS) Waters Acquity-Waters Xevo TQ-S. Analytical column Acquity BEH C18 100×2.1 mm, 1.7 μm. Mobile phase A: 20 mM NH$_4$-Formate+0.2% formic acid. Mobile phase B: Acetonitrile+0.2% formic acid. Gradient run from 95/5% to 5/95% in 11.0 min. Flow rate 0.3 mL/min. MRM monitoring of test item and the added analytical standards.

Dosing and blood sampling for compounds (Id-ia), (Id-ib), (Id-iia) and (Id-iib): Han Wistar rats were supplied by Charles River Laboratories, Wiga GmbH, Germany. An artificial, automatically controlled, light and dark cycle of 12 hours was maintained. The rats received a standard laboratory diet from Brogaarden (Altromin 1324 pellets). The rats had unrestricted access to the diet. Male Han Wistar rats were dosed a single oral gavage administration of (Id-ia), (Id-ib), (Id-iia) and (Id-iib) respectively, orally by gavage. Rats were given 633 μg/kg (Id-ia) and (Id-ib)) or 392 μg/kg (Id-iia) and (Id-iib)), blood samples from 3 male animals were collected on the following time points at Day 1: 1, 2, 4, 6, 8, and 24 hours after dosing.

Dosing and blood sampling for compounds (Ic), (Id-iab) and (Id-iiab): Han Wistar rats were supplied by Envigo, UK. An artificial, automatically controlled, light and dark cycle of 12 hours was maintained. The rats received a standard laboratory diet Teklad 2014C. The rats had unrestricted access to the diet. Male Han Wistar rats were dosed a single oral gavage administration of (Ic), (Id-iab) and (Id-iiab), respectively, orally by gavage. Rats were given 793 μg/kg (Id-iab), 703 μg/kg (Id-iiab) and 494 μg/kg (Ic). Blood samples from 3 male animals were collected on the following time points at Day 1: 1, 2, 4, 6, 8, and 24 hours after dosing Instrumentation Used for Analysis Apomorphine from Dosing Apomorphine and the Corresponding Glucuronide Conjugate: (((2S,3S,4S,5R,6S)-6-[[(6aR)-11-hydroxy-6-methyl-5,6,6a,7-tetrahydro-4H-dibenzo[de,g]quinolin-10-yl]oxy]-3,4,5-trihydroxy-tetrahydropyran-2-carboxylic acid, and sulfate conjugates: [(6aR)-11-hydroxy-6-methyl-5,6,6a,7-tetrahydro-4H-dibenzo[de,g]quinolin-10-yl] hydrogen sulfate, and [(6aR)-10-hydroxy-6-methyl-5,6,6a,7-tetrahydro-4H-dibenzo[de,g]quinolin-11-yl] hydrogen sulfate):

Mass spectrometer (UPCLC-MS/MS) Waters Acquity I-Class-Waters Xevo TQ-S. Analytical column Acquity HSS T3 C18 50×2.1 mm, 1.8 μm. Mobile phase A: 10 mM NH$_4$—Formate 0.2% formic acid:Acetonitril (95:5). Mobile phase B: 10 mM NH$_4$-Formate 0.2% formic acid:Acetonitril (5:95). Gradient run from 95/5% to 5/95% in 2.40 min. Flow rate 0.3 mL/min. MRM detection of test items and the added analytical standards Dosing and blood sampling: Han Wistar rats were supplied by Charles River Laboratories, Wiga GmbH, Germany. An artificial, automatically controlled, light and dark cycle of 12 hours was maintained. The rats received a standard laboratory diet from Brogaarden (Altromin 1324 pellets). The rats had unrestricted access to the diet. Male Han Wistar rats were administered a single dose of apomorphine either subcutaneously or orally by gavage, or administered a single dose of apormorphine conjugates orally by gavage. From rats administered 3000 μg/kg (apomorphine) or 3899 μg/kg (sulfate conjugate) or 4977 μg/kg (glucuronide conjugates), blood samples from 3 male animals were collected on the following time points at Day 1: 0.25, 0.5, 1, 2, 4 and 8 hours SC administration and 0.5, 1, 2, 4, 8 and 24 h PO administration after dosing.

TABLE 3

PK parameters for (4aR,10aR)-1-n-Propyl-1,2,3,4,4a,5,10,10a-octahydro-benzo[g]quinoline-6,7-diol (compound (I)) after oral dosing of 0.300 mg/kg (Ia), 0.300 mg/kg (Ib), 0.633 mg/kg of (Id-ia) 0.633 mg/kg of (Id-ib), 0.392 mg/kg of (Id-iia), 0.392 mg/kg (Id-iib), 793 µg/kg (Id-iab), 703 µg/kg (Id-iiab) and 494 µg/kg (Ic) to Wistar rats according to Example 4.

|  | compound | $T_{max}$ (h) | $C_{max}$ (pg/mL) | $AUC_{0-24}$ (pg*h/mL) | $t_{1/2}$ (h) | 24 h exposure (pg/mL) |
|---|---|---|---|---|---|---|
| Prior art prodrugs | (Ia) | 1.0 | 3160 | 13600 | 4.09 | 48 ± 26 |
|  | (Ib) | 0.5 | 4990 | 31000 | N/A | 147 ± 28 |
|  | (Ic) | 1.0 | 14 | 104 | N/A | N/A |
| Compounds of the invention | (Id-ia) | 4.0 | 1350 | 15500 | 6.8 | 208 ± 89 |
|  | (Id-ib) | 4.0 | 2150 | 21100 | 7.1 | 270 ± 112 |
|  | (Id-iia) | 6.0 | 945 | 11300 | 7.7 | 192 ± 14 |
|  | (Id-ib) | 8.0 | 665 | 7800 | 8.0 | 166 ± 94 |
|  | (Id-iab) | 4.0 | 964 | 18900 | N/A | 800 ± 244 |
|  | (Id-iiab) | 24 | 68 | 1040 | N/A | 68 ± 38 |

EXAMPLE 5

PK Experiments in Minipigs

Blood samples of approximately 0.5 mL was drawn from the V. jugularis via a syringe and put into precooled EDTA tubes with stabilizing solution as described for rats in example 4. Concentrations of the compounds were measured in plasma. Plasma samples were analyzed by solid phase extraction or direct protein precipitation followed by UPLC-MS/MS. MS detection using electrospray in the positive ion mode with monitoring of specific mass-to-charge transitions for the compound in question using internal standards for correcting the response. The concentration-time data was analyzed, using standard software using appropriate one compartmental techniques to obtain estimates of the derived PK parameters.

Instrumentation Used for Analysis of Compound (I) from Dosing of Compounds (Id-ia), (Id-ib), (Id-iia) and (Id-iib).

Mass spectrometer (LC-MS/MS) Waters Acquity-Waters Xevo TQ-S. Analytical column Acquity BEH C18 100×2.1 mm, 1.7 µm. Mobile phase A: 20 mM $NH_4$-Formate+0.2% formic acid. Mobile phase B: Acetonitrile+0.2% formic acid. Gradient run from 95/5% to 95/5 in 11.0 min. Flow rate 0.3 mL/min. MRM monitoring of test item and the added analytical standards.

Dosing and blood sampling from single dose pharmacokinetic study in female Ellegaard Gottingen minipig supplied by Ellegaard, DK. An artificial, automatically controlled, light and dark cycle of 12 hours was maintained. The minipigs received a standard laboratory diet from Brogaarden (Altromin pellets). The minipigs had unrestricted access to the diet. The minipigs were administered compounds (Id-ia), (Id-ib), (Id-iia) and (Id-iib), respectively, orally by gavage. Minipigs were dosed with 160 µg/kg of compounds (Id-ia) and (Id-ib), respectively or 80 µg/kg of compounds (Id-iia) and (Id-iib), respectively, blood samples from 3 female animals were collected on the following time points at Day 1: 1, 2, 4, 6, 8, 12 and 24 hour after dosing.

TABLE 4

PK parameters for (4aR,10aR)-1-n-Propyl-1,2,3,4,4a,5,10,10a-octahydro-benzo[g]quinoline-6,7-diol (compound (I)) after oral dosing of 0.160 mg/kg of (Id-ia) 0.160 mg/kg of (Id-ib), 0.050 mg/kg (Id-iia), 0.050 mg/kg (Id-iib) to Minipigs according to Example 5.

| compound | $T_{max}$ (h) | $C_{max}$ (pg/mL) | $AUC_{0-24}$ (pg*h/mL) |
|---|---|---|---|
| (Id-ia) | 8.0 | 1120 | 13000 |
| (Id-ib) | 5.3 | 1300 | 14300 |
| (Id-iia) | 7.3 | 501 | 6280 |
| (Id-ib) | 12 | 328 | 4160 |

EXAMPLE 6

PK/PD of Compound (Id-ia)/Compound (I) in Rat Hyperactivity Assay

Animals

In total, 206 male CD rats (Charles River, Germany) weighing 200-250 grams (165-190 grams upon arrival) were used in the study. Animals were housed at a standard temperature (22±1° C.) and in a light-controlled environment (lights on from 7 am to 8 pm) with ad libitum access to food and water. The experiment described below was performed in accordance with the standard operating procedures of Charles River Discovery Research Services Finland Ltd. and in accordance with the national Animal Experiment Board of Finland (Eläinkoelautakunta, ELLA) authority on animal testing.

Locomotor Activity Testing, Open Field

The test device is a square Plexiglass-arena (measuring 40×40×40 cm), in which the movement paths of the rats are recorded by an activity monitor (Med. Associates Inc.). Before the test period is initiated, rats are habituated to their test cage for 60 minutes. Upon completion of habituation, animals were treated with either compound or vehicle and placed back into the open field apparatus. The main test parameter measured is ambulatory distance (recorded in 5 minute segments). Overall time of measurement after receiving initial treatment was 360 minutes. Total follow up period in the study was 420 min, including 60 min of habituation.

Results

Oral administration of compound (Id-ia) was assessed in the rat locomotor activity assay, and this functional readout was then correlated to plasma concentrations of compound (I). Apomorphine and pramipexole were also concomitantly tested in this assay as comparators (i.e. known standard-of-care (SoC) in the Parkinson's Disease field), and plasma concentration was analyzed for apomorphine.

As shown in FIG. 3, compound (Id-ia) (10 to 300 μg/kg, p.o.) increases locomotor activity with an effect starting approximatively 2 hours' post-administration (around the 180-minute time point) and lasting until the end of recording (at the 415-minute time point). In contrary, the hyperactivity induced by apomorphine (3 mg/kg, s.c.) is immediate but short-lasting as the effect is gone 1.5 hours. post administration (at the 150-minuite time point). Pramipexole (0.3 mg/kg, s.c.) also induces an increase in activity, but its effect appears about 1 hour post administration and is gone 2.5 hours later (at the 270-minute time point). The total distance travelled as seen in FIG. 4 demonstrates a significantly increased activity for both compound (Id-ia) and the two comparators tested, and this effect is the one that is to be expected from dopamine agonists.

Figure 6:
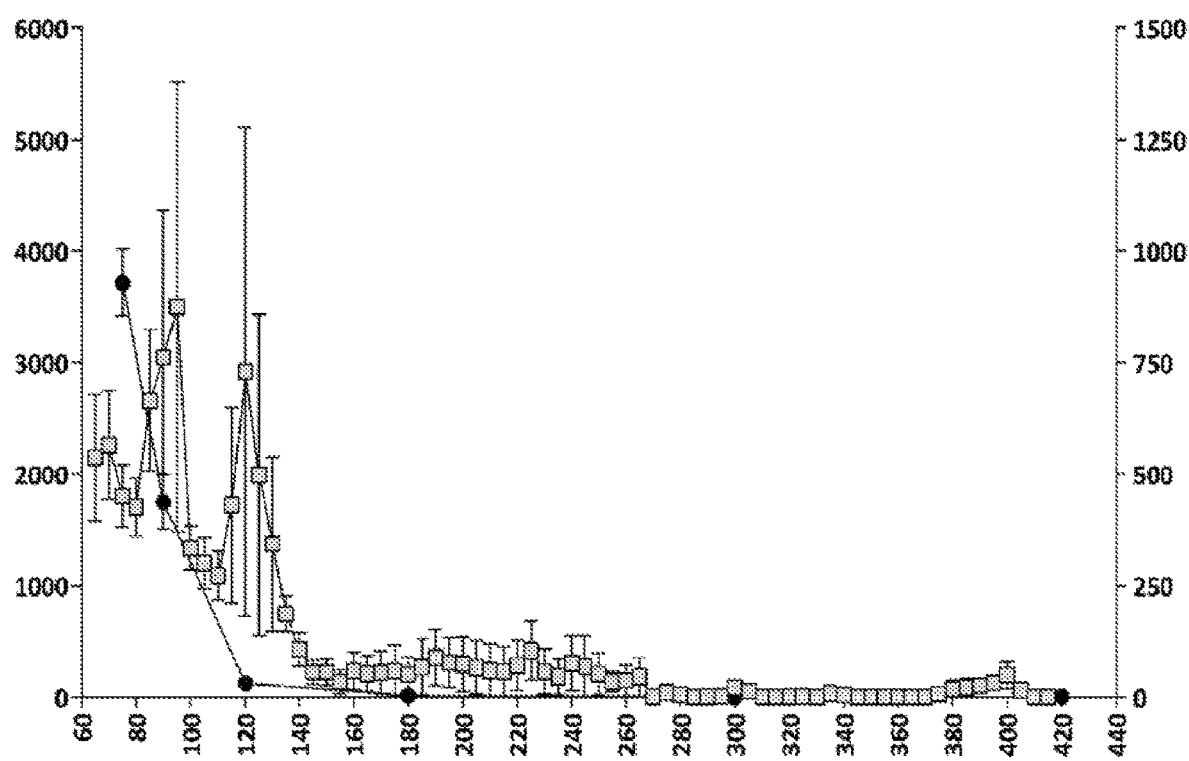

In parallel with the locomotor activity assessment, plasma samples were taken from satellite animals at 6 different time points (0.5, 1, 2, 3, 4 & 6 hour's post-dose for animals treated with compound (Id-ia)). Pharmacokinetic analysis demonstrates that the behavioral effects of compound (Id-ia) (100 μg/kg, p.o.) correlate with the plasma concentrations of compound (I) (see FIG. 5), demonstrating that the behavioral effect of compound (Id-ia) is driven by Compound (I) rather than by Compound (Id-ia) itself. The corresponding exposure analysis of apomorphine (at 0.25, 0.5, 1, 2, 4 & 6 hour's post-dose) resulted in a correlation between plasma concentrations of apomorphine and hyperactive behavior (see FIG. 6).

The invention claimed is:

1. A method for the treatment of a neurodegenerative disease selected from Parkinson's Disease, Huntington's disease, Restless leg syndrome and Alzheimer's disease; or a neuropsychiatric disease or disorder selected from schizophrenia, attention deficit hyperactivity disorder and drug addiction; wherein said method comprises administering to a patient in need thereof a pharmaceutical composition comprising a compound according to formula (Id):

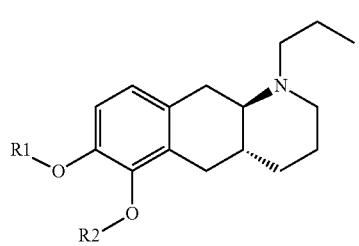

(Id)

or a pharmaceutically acceptable salt thereof, wherein:

R1 is H and R2 is substituent (i) below; or
R1 is substituent (i) below and R2 is H; or
R1 and R2 are both represented by substituent (i) below;

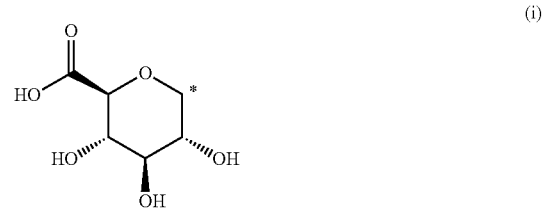

(i)

wherein * indicates the attachment point; and wherein the carbon atom at the attachment point on substituent (i) is in the S-configuration;

and one or more pharmaceutically acceptable excipients.

2. The method according to claim 1, wherein the compound or pharmaceutically acceptable salt thereof is selected from the group consisting of:

(Id-ia): (2S,3S,4S,5R,6S)-3,4,5-trihydroxy-6-(((4aR,10aR)-7-hydroxy-1-propyl-1,2,3,4,4a,5,10,10a-octahydrobenzo[g]quinolin-6-yl)oxy)tetrahydro-2H-pyran-2-carboxylic acid;

(Id-ib): (2S,3S,4S,5R,6S)-3,4,5-trihydroxy-6-(((4aR,10aR)-6-hydroxy-1-propyl-1,2,3,4,4a,5,10,10a-octahydrobenzo[g]quinolin-7-yl)oxy)tetrahydro-2H-pyran-2-carboxylic acid; and (Id-iab): (2S,2'S,3S,3'S,4S,4'S,5R,5'R,6S,6'S)-6,6'-(((4aR,10aR)-1-propyl-1,2,3,4,4a,5,10,10a-octahydrobenzo[g]quinoline-6,7-diyl)bis(oxy))bis(3,4,5-trihydroxytetrahydro-2H-pyran-2-carboxylic acid);

or a pharmaceutically acceptable salt of any of these compounds.

3. The method according to claim 1, wherein said compound or pharmaceutically acceptable salt thereof is the compound represented by formula (Id-ia) below:

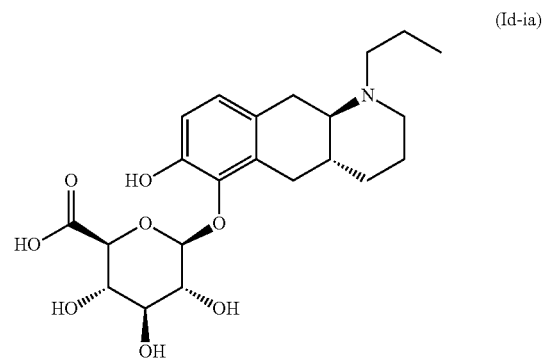 [SMILES: CCCN1CCC[C@@H]2Cc3c(ccc(O)c3O[C@@H]3O[C@H](C(=O)O)[C@@H](O)[C@H](O)[C@H]3O)C[C@H]21]

(Id-ia)

or a pharmaceutically acceptable salt thereof.

4. The method according to claim 1, wherein said compound or pharmaceutically acceptable salt thereof is the compound represented by formula (Id-ib) below:

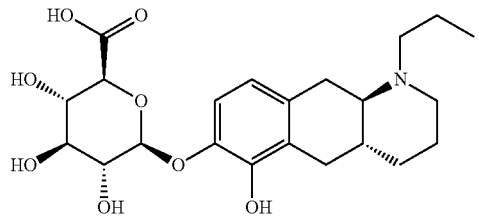

(Id-ib)

or a pharmaceutically acceptable salt thereof.

5. The method according to claim 1, wherein said compound or pharmaceutically acceptable salt thereof is the compound represented by formula (Id-iab) below:

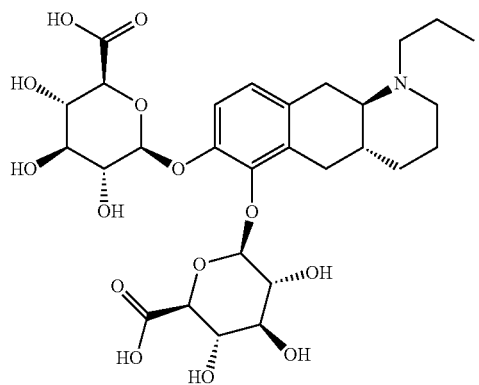

(Id-iab)

or a pharmaceutically acceptable salt thereof.

6. The method according to claim 1, wherein said pharmaceutical composition is free of the compound of formula (I):

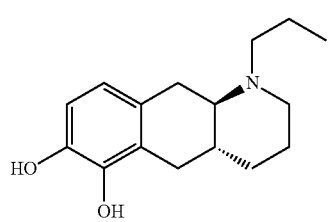

(I)

7. The method according to claim 1, wherein said compound or pharmaceutically acceptable salt thereof is in a solid form.

8. The method according to claim 1, wherein the pharmaceutical composition comprises a pharmaceutically acceptable salt of the compound according to formula (Id).

9. The method according to claim 1, wherein the pharmaceutical composition comprises a pharmaceutically acceptable salt of:

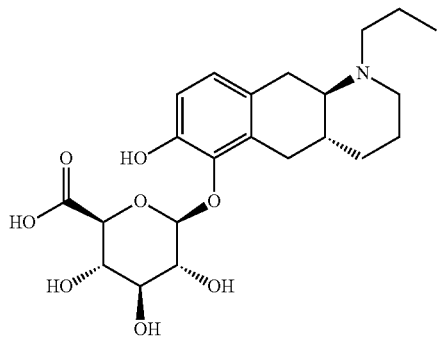 [SMILES: CCCN1CCC[C@@H]2Cc3c(ccc(O)c3O[C@@H]3O[C@H](C(=O)O)[C@@H](O)[C@H](O)[C@H]3O)C[C@H]21]

(Id-ia) ((2S,3S,4S,5R,6S)-3,4,5-trihydroxy-6-(((4aR,10aR)-7-hydroxy-1-propyl-1,2,3,4,4a,5,10,10a-octahydrobenzo[g]quinolin-6-yl)oxy)tetrahydro-2H-pyran-2-carboxylic acid);

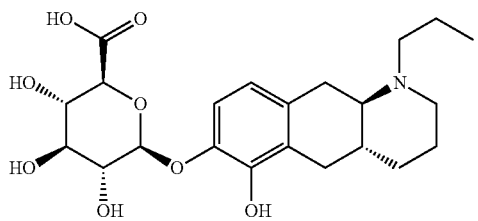 [SMILES: CCCN1CCC[C@@H]2Cc3c(ccc(O[C@@H]4O[C@H](C(=O)O)[C@@H](O)[C@H](O)[C@H]4O)c3O)C[C@H]21]

(Id-ib) ((2S,3S,4S,5R,6S)-3,4,5-trihydroxy-6-(((4aR,10aR)-6-hydroxy-1-propyl-1,2,3,4,4a,5,10,10a-octahydrobenzo[g]quinolin-7-yl)oxy)tetrahydro-2H-pyran-2-carboxylic acid); or

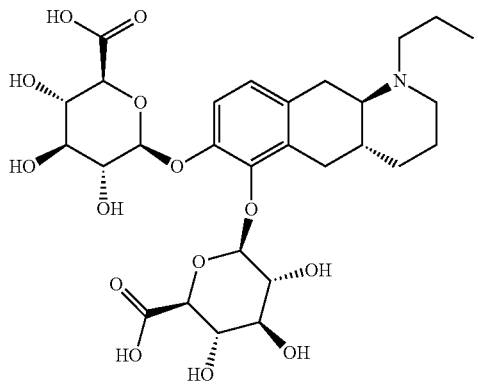 [SMILES: CCCN1CCC[C@@H]2Cc3c(ccc(O[C@@H]4O[C@H](C(=O)O)[C@@H](O)[C@H](O)[C@H]4O)c3O[C@@H]3O[C@H](C(=O)O)[C@@H](O)[C@H](O)[C@H]3O)C[C@H]21]

(Id-iab) ((2S,2'S,3S,3'S,4S,4'S,5R,5'R,6S,6'S)-6,6'-(((4aR,10aR)-1-propyl-1,2,3,4,4a,5,10,10a-octahydrobenzo[g]quinoline-6,7-diyl)bis(oxy))bis(3,4,5-trihydroxytetrahydro-2H-pyran-2-carboxylic acid)).

10. The method according to claim 1, wherein said pharmaceutical composition is for oral administration.

11. The method according to claim 10, wherein said pharmaceutical composition for oral administration is a tablet or a capsule.

12. The method according to claim 1, wherein the method is for treatment of Parkinson's Disease.

13. The method according to claim 1, wherein the patient is a human being.

14. The method according to claim 3, wherein said pharmaceutical composition is free of the compound of formula (I):

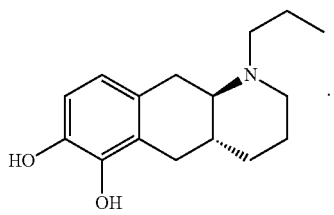
(I)

15. The method according to claim 4, wherein said pharmaceutical composition is free of the compound of formula (I):

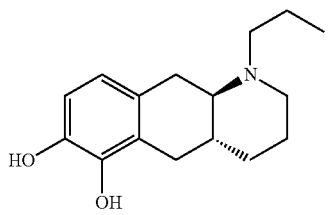
(I)

16. The method according to claim 5, wherein said pharmaceutical composition is free of the compound of formula (I):

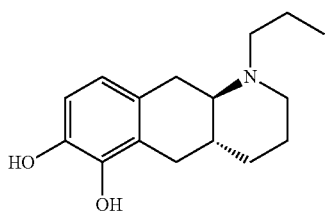
(I)

17. The method according to claim 3, wherein the method is for treatment of Parkinson's Disease.

18. The method according to claim 4 wherein the method is for treatment of Parkinson's Disease.

19. The method according to claim 5, wherein the method is for treatment of Parkinson's Disease.

20. The method according to claim 1, wherein the pharmaceutical composition comprises a therapeutically effective amount of the compound according to formula (Id) or a pharmaceutically acceptable salt thereof.

* * * * *